US006780418B1

(12) United States Patent
Fahey et al.

(10) Patent No.: US 6,780,418 B1
(45) Date of Patent: Aug. 24, 2004

(54) REAGENTS AND IMMUNOASSAY FOR THE DETECTION AND QUANTITATIVE DETERMINATION OF MYCOTHIOL AND PRECURSORS THEREOF

(75) Inventors: Robert C. Fahey, Del Mar, CA (US); Gerald L. Newton, San Diego, CA (US); Maria Margarita D. Unson, Kailua-Kona, HI (US); Charles E. Davis, San Diego, CA (US); Sara J. Anderberg, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/530,370

(22) PCT Filed: Oct. 23, 1998

(86) PCT No.: PCT/US98/22577

§ 371 (c)(1),
(2), (4) Date: Jul. 6, 2000

(87) PCT Pub. No.: WO99/21580

PCT Pub. Date: May 6, 1999

Related U.S. Application Data

(60) Provisional application No. 60/063,620, filed on Oct. 27, 1997.

(51) Int. Cl.[7] .................. A61K 39/04; A61K 39/40; C07D 277/62; C07C 53/00
(52) U.S. Cl. ................ 424/248.1; 424/164.1; 424/168.1; 435/252.1; 435/253.1; 548/174; 554/101
(58) Field of Search ............... 424/164.1, 168.1, 424/248.1; 435/252.1, 253.1; 548/174; 554/101

(56) References Cited

PUBLICATIONS

Newton et al., "Distribution of Thiols in Microorganisms: Mycothiol Is a Major Thiol in Most Actinomycetes," *Journal of Bacteriology* 178(7):1990–1995 (Apr. 1996).

Spies and Steenkamp, "Thiols of intracellular pathogens; Identification of ovothiol A in *Leishmania donovani* and structural analysis of a novel thiol from *Mycobacterium bovis,*" *Eur. J. Biochem.* 224:203–213 (1994).

Unson et al., "An immunoassay for the detection and quantitative determination of mycothiol," *Journal of Immunological Methods* 214:29–39 (1998).

*Primary Examiner*—Rodney P Swartz
(74) *Attorney, Agent, or Firm*—Gray Cary Ware & Freidenrich, LLP

(57) ABSTRACT

A method of detecting a member of the taxa actinomycetos is provided. A method also is provided for detecting mycothiol or precursor thereof. An antibody is provided which binds to mycothiol or a mycothiol precursor. A method is further provided for diagnosis of a subject having or at risk of having an actinomycetes-associated disorder. A method is also provided for identifying a sample with altered production of mycothiol or a precursor thereof. A method is provided for detecting mycothiol or precursor thereof in a bacterial colony. Kits are also disclosed which are useful for detecting the presence of mycothiol or precursor thereof in a sample.

10 Claims, 12 Drawing Sheets

REAGENTS AND IMMUNOASSAY FOR THE DETECTION AND QUANTITATIVE DETERMINATION OF MYCOTHIOL AND PRECURSORS THEREOF

CROSS-REFERENCE TO RELATED APPLICATION

This application claims priority from U.S. Provisional Application Serial No. 60/063,620, filed Oct. 27, 1997.

STATEMENT AS TO FEDERALLY SPONSORED RESEARCH

This invention was made with partial Government support under Grant No. A136971, award by The National Institutes of Allergy and Infectious Disease and Grant No. AA11393 from the National Institute of Alcohol Abuse and Alcoholism. The government may have certain rights in the invention.

FIELD OF THE INVENTION

This invention relates generally to the field of detection of bacteria, and more specifically to the diagnosis of actinomycetes infection, particularly to those caused by mycobacteria. The invention also relates generally to the field of diagnosis of bacterial infection, and more specifically to the diagnosis of diseases associated with actinomycetes infection such as tuberculosis.

BACKGROUND OF THE INVENTION

Human tuberculosis is caused primarily by the bacterium *Mycobacterium tuberculosis*. Although other species of mycobacteria can cause human disease, *M. tuberculosis* is by far the most important cause of morbidity and mortality among the mycobacterial genus. It is estimated that 8.8 million new cases of tuberculosis occurred in 1995 and these numbers are projected to continue to increase.

The laboratory diagnosis of tuberculosis has always been complicated by the slow growth of *M. tuberculosis* in culture. Visible growth on solid culture media can require up to 8 weeks of incubation. Presumptive diagnoses are based on finding mycobacteria by microscopic examination of a diagnostic specimen often an expectorated sputum. These smears are either stained by acid fast stains like the Ziehl-Neelsen stain or by auramine-rhodamine staining followed by fluorescence microscopy. Smears must contain $5 \times 10^3$ to $10^5$ bacteria per ml for detection and are nonspecific since they recognize all species of mycobacteria (Nolte, F. S., and Metchock, B., 1995, "Mycobacterium." In: *Manual of Clinical Microbiology*, 6th Edition., Murray, P. R. (ed.), ASM Press, Washington, D.C.) Definitive diagnosis is dependent on the isolation and identification of *M. tuberculosis* in culture of a diagnostic specimen, usually a sputum obtained from a patient with a productive cough (Nolte and Metchock, 1995, supra). Although the use of liquid cultures with radiometric detection methods and the identification of cultivated bacteria by nucleic acid probes have shortened the time to isolate and identify *M. tuberculosis*, definitive diagnosis still usually requires 2–3 weeks (Raviglione, M. D., and O'Brien, R. J., 1998, "Tuberculosis," In: *Harrison's Principles of Internal Medicines*, 14th Edition, Fauci et al., eds., McGraw-Hill, N.Y.).

The conventional technique for detecting tuberculosis is by microscopic identification of the bacteria in patient specimens treated with special stains combined with cultivation on specific bacteriologic media. Detection by the staining techniques is nonspecific and relatively insensitive, and cultivation is time-consuming and expensive because *Mycobacterium tuberculosis* grows very slowly. Detection of *M. tuberculosis* by nucleic acid amplification is an adjunctive approach. Because of the duration of time required to establish a definitive diagnosis, many adjunctive laboratory diagnostic tests have been investigated. Serologic detection of antibody to *M. tuberculosis* has had very low predictive values (Daniel, T. M., and Debanne, S. M., 1987, *Am. Rev. Respir. Dis.* 158:678). Serologic detection of tuberculostearic acid, another unique component of actinomycetes, by gas chromatography and mass spectroscopy with selective ion monitoring has been too costly to be implemented outside of research laboratories (Brooks et al., 1990, *J. Clin. Microbiol.* 28:98; Nolte and Metchock, 1995, supra).

Mycothiol (MSH) is a recently discovered novel cysteine derivative produced only by actinomycetes. Among the actinomycetes, mycobacteria produce mycothiol in the greatest amounts. Mycobacteria are the main group of actinomycetes that infect humans. Among these infections are tuberculosis (TB), as well as other mycobacterial infections. Other genera of actinomycetes (corynebacteria, including the causative agent of diphtheria, and Nocardia species, which cause pulmonary nocardiosis) make MSH, but they are minor causes of human morbidity and mortality compared to tuberculosis (Newton et al., 1996, *J. Bacteriol.*, 178).

The available information on mycothiol is quite limited and very recent. The structure for mycothiol, 1-D-myo-inosityl-2-(N-acetyl-L-cysteinyl)amido-2-deoxy-α-D-glucopyranoside (MSH) (FIG. 1), was first reported by Sakuda et al. (1994, *Biosci. Biotech. Biochem.*, 58:1347) who isolated it as its disulfide from a Streptomyces species. It was later isolated as the free thiol from *Mycobacterium bovis* (Spies, H. S. C., and Steenkamp, D. J., 1994, *Eur. J. Biochem.*, 224:203) and *Streptomyces clavuligerus* (Newton et al., 1995, *Eur. J. Biochem.*, 230:821). The name "mycothiol" (Spies and Steenkamp, 1994, supra) and the abbreviation MSH (Newton et al., 1995, supra) have been proposed for this unusual thiol.

The actinomycetes do not produce glutathione (GSH), a thiol antioxidant found in many prokaryotes and eukaryotes (Fahey, R. C., and Sundquist, A. R., 1991, *Adv. Enzymol. Relat. Areas Mol. Biol.* 64:1). Instead, most actinomycetes (but not other prokaryotes or eukaryotes) produce MSH at millimolar levels (Newton et al., 1996, *J. Bacteriol.*, 178:1990–1995). MSH has superior antioxidant properties to GSH (Newton et at., 1995, supra) and thus may serve both as a stable intracellular storage form of cysteine and as the essential cofactor for oxidative stress-response and detoxification enzymes in a manner analogous to that of GSH in GSH-producing organisms. Though little is currently known about the biochemistry of MSH, it has recently been reported that MSH is the cofactor for an NAD/"cofactor"-dependent formaldehyde dehydrogenase found in actinomycetes, where it serves in a detoxification role analogous to that of GSH in the NAD/GSH-dependent formaldehyde dehydrogenase of cukaryotes and Gram-negative bacteria (Misset-Smits, M., et al., 1997, *FEBS Lett.* 409:221–222). It is likely that further examples of MSH-dependent protective enzymes will be found in the future. Thus enzymes involved in the metabolism of MSH may represent targets for new drugs directed against tuberculosis and other mycobacterial infections (Newton et al., 1996, supra).

Among the actinomycetes, mycobacteria produce the highest levels of mycothiol, ~5 million molecules per cell, and as few other actinomycetes besides mycobacteria are human pathogens, the present inventors have thus proposed that detection of MSH is a possible way to screen for tuberculosis and other mycobacterial infections. The development of sensitive and specific methods for the detection of MSH is essential for both research in the elaboration of mycothiol metabolism and for use in clinical diagnosis of mycobacterial infection. MSH analysis has previously relied on derivatization with thiol-specific fluorescent labeling reagents followed by HPLC analysis (Spies and Steenkamp, 1994, supra; Newton et al., 1993, *J. Bacteriol.*, 175:2734), but this methodology is expensive, time-consuming, lacks the sensitivity needed to be clinically useful in the diagnosis of mycobacterial infection, and lacks the versatility needed for a variety of applications such as the screening for mycothiol production by bacterial colonies.

SUMMARY OF THE INVENTION

The present invention is based on the discovery of methods for detecting mycothiol, a recently described novel cysteine derivative produced at millimolar intracellular levels by actinomycetes, including the pathogenic mycobacteria.

A method of detecting a member of the taxa actinomycetes is provided. The method includes incubating a reagent that detects mycothiol or a precursor thereof with a sample for a time sufficient for said reagent to react with mycothiol or precursor thereof, and detecting the reaction of the reagent with mycothiol or a precursor thereof. In this method detection of a reaction is indicative of the presence of a member of the taxa actinomycetes.

An antibody is provided which binds to mycothiol or a mycothiol precursor. The antibody may be a monoclonal or a ployclonal antibody.

A method is provided for diagnosis of a subject having or at risk of having an Actinomycetes-associated disorder. The method includes contacting a sample from the subject having or at risk of having an actinomycetes-associated disorder with a reagent that detects mycothiol or precursor thereof for a period of time sufficient for said reagent to react, and detecting the reaction of the reagent with mycothiol or precursor thereof. The reaction of the reagent that detects mycothiol or precursor thereof to the sample is compared to a control sample.

A method is provided for identifying a sample with altered production of mycothiol or a precursor thereof, including contacting a test sample with a reagent that detects mycothiol or precursor thereof for a period of time sufficient for the reagent to react, and detecting the reaction of the reagent with mycothiol or precursor thereof. The reagent that detects mycothiol or precursor thereof to the test sample is compared with a control sample; a difference in the amount of reaction with the test sample as compared to the control sample is indicative of an alteration in the production of mycothiol or precursor thereof.

A method is provided for detecting mycothiol or precursor thereof in a bacterial colony, including contacting a membrane to a bacteria plated on a bacterial culture plate for a time sufficient to allow the bacteria to adhere to the membrane and lysing the bacteria. The method also includes contacting the membrane with a reagent to detect mycothiol or precursor thereof, and detecting said the reaction of reagent with mycothiol or precursor thereof.

A method is further provided for detecting mycothiol or precursor thereof including biotinylating mycothiol or precursor thereof to form biotinylated mycothiol or biotinylated mycothiol precursor, and contacting the biotinylated mycothiol or biotinylated mycothiol precursor to an antibody with binds mycothiol or precursor thereof to form a complex. The method further includes detecting the presence of said complex with a detection reagent.

Kits are also disclosed which are useful for detecting the presence of mycothiol or precursor thereof in a sample.

A method is also provided for detecting a mycothiol or a precursor thereof, including partially purifying mycothiol or a precursor thereof, reacting the precursor of mycothiol with a reagent for fluroescent amine labeling to form a reaction product; and detecting the presence of the reaction product. Detecting may be at a pH range from about 7.5 to 9, and more likely from about 8.0 to 8.6.

DETAILED DESCRIPTION OF THE INVENTION

The present invention relates to mycothiol and precursors of mycothiol, and to reagents for the detection of mycothiol and precursors thereof including antibodies and chemical reagents. These methods and reagents are useful for the diagnosis and treatment of actinomycetes-associated disorders, including mycobacteria-associated disorders such as tuberculosis.

It must be noted that as used herein and in the appended claims, the singular forms "a," "and," and "the" include plural referents unless the context clearly dictates otherwise. Thus, for example, reference to "a cell" includes a plurality of such cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, antibodies, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue or prior invention.

The invention provides methods for detecting a member of the taxa actinomycetes, by incubating a reagent that detects mycothiol or precursor thereof with a sample for a time sufficient for the reagent to react with mycothiol or precursor thereof. The reaction of the reagent with mycothiol or precursor thereof is then detected. Detection of a reaction is indicative of the presence of a member of the taxa actinomycetes.

Figure 1:
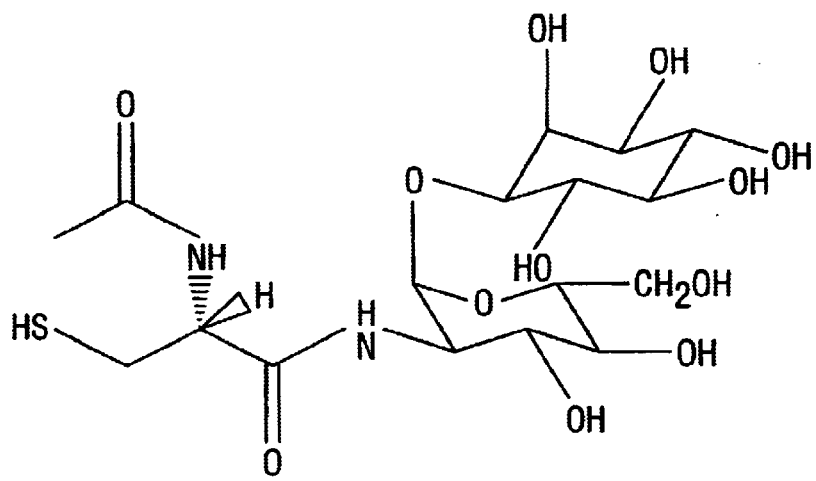
FIG. 1 shows the structure and names (including abbreviations) for mycothiol.

"Mycothiol" or "MSH" or "AcCys-GlcN-Ins" is 1-D-myo-inosityl-2-(N-acetyl-L-cysteinyl)amido-2-deoxy-α-D-glucopyranoside. The structure of mycothiol is shown in FIG. 1. A "mycothiol precursor" is a molecule from which mycothiol can be produced. Examples of mycothiol precursors include N-acetyl-cysteine (AcCys), 2-(N-acetyl-L cysteinyl) amido-2-deoxy-α-D-glucopyanoside (AcCys-GlcN), 1-D-myo-inosityl-2-amino-2-deoxy-α-D-glycopyranoside (GlcN-Ins), 1-D-myo-inosityl-2-(L-cysteinyl)amido-2-deoxy-D-glucopyanoside (Cys-GlcN-Ins) and 2-(L-cysteinyl)amido-2-deoxy-D-glucopyanoside (Cys-GlcN). In one embodiment, precursors of mycothiol are GlcN-Ins, Cys-GlcN-Ins, and AcCys. Mycothiol is produced at millimolar levels by the taxa actinomycetes. The genus Mycobacteria is a member of the taxa actinomycetes that colonizes humans, and are a causative agent in disease (e.g., tuberculosis). It should be noted that an assay of mycothiol that assesses the production of myocothiol in the reduced thiol form is useful in distinguishing viable actinomycetes from non-viable actinomycetes. A "viable" actinomycete is a cell that is metabolically active and which carries out the biochemical processes required for the cell.

A "reagent that detects mycothiol or precursor" is any molecule that reacts with mycothiol when incubated with mycothiol. "Reacting" includes binding, such as an antibody binding an antigen, or the binding of a fluorescent molecule with mycothiol such that the fluorescent properties of a molecule are altered. "Reacting" also includes chemically reacting such that covalent bonds are modified. "Reacting" further includes reacting such that hydrogen bonds are modified. "Incubating" includes conditions which allow contact between the reagent that detects mycothiol or a precursor thereof with a sample. "Contacting" includes in solution and solid phase. One of skill in the art can readily determine the time sufficient for the reagent to react with mycothiol or precursor thereof. A "sample" is any substance which might possibly contain mycothiol or a precursor thereof. In one embodiment the sample is a patient sample, such as a blood sample, a serum sample, a urine sample, a fecal sample, a tissue biopsy, a cerebrospinal fluid sample, a pleural fluid sample, an ascites sample, and a sputum sample, in another embodiment, the sample is a bacterial sample, such as a culture of a bacterium in a growth medium.

"Detection" is performed by any means suitable to identify the interaction of the reagent with mycothiol or precursor thereof. In one embodiment, when the reagent is a chemical reagent, physical or chemical parameters of the reagent or the products of the interaction of the agent with mycothiol can be monitored. In another embodiment, when the reagent is an antibody, the antibody can be detectably labeled. Detectable labels are well known in the art, and include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Alternatively, when the reagent is an antibody, detection can be performed using a second antibody which is detectably labeled which recognizes the antibody that binds mycothiol or precursor thereof. The antibody may also be biotinylated, and a second avidinated label used to determine the presence of the biotinylated reagent which detects mycothiol or precursor thereof.

Antibodies

The term "antibody" stands for an immunoglobulin protein which is capable of binding an antigen. Antibody as used herein is meant to include the entire antibody as well as any antibody fragments (e.g., F(ab', Fab, Fv) capable of binding the epitope, antigen or antigenic fragment of interest (see below). Preferred antibodies for assays of the invention are immnunoreactive or immunospecific for and therefore specifically and selectively bind to mycothiol or precursor thereof. The term "antibody" encompasses all types of antibodies, e.g., polyclonal, monoclonal, and those produced by the phage display methodology. Particularly preferred antibodies of the invention are antibodies which have a relatively high degree of affinity for mycothiol or precursor thereof.

Mycothiol or precursor thereof can be used to produce antibodies which are immunoreactive or bind to mycothiol or precursor thereof. Antibodies which consist essentially of pooled antibodies with different epitopic specificities, as well as distinct monoclonal antibody preparations are provided. "Purified antibody" refers to that which is sufficiently free of other proteins, carbohydrates, and lipids with which it is naturally associated. Such an antibody "preferentially binds" to mycothiol or a precursor thereof, and does not substantially recognize or bind to other antigenetically unrelated molecules. By "binds specifically" is meant high avidity and/or high affinity binding of an antibody to a specific molecule, e.g., mycothiol or a precursor thereof. Antibody binding to its epitope on a specific molecule is preferably stronger than binding of the same antibody to any other molecule, particularly those which may be present in molecules in association with, or in the same sample.

The preparation of polyclonal antibodies is well-known to those skilled in the art. See, for example, Green et al, "Production of Polyclonal Antisera," in: *Immunochemical Protocols* pages 1–5, Manson, ed., Humana Press 1992; Coligan et al, "Production of Polyclonal Antisera in Rabbits, Rats, Mice and Hamsters," in: *Current Protocols in Immunology*, section 2.4.1, 1992, which are hereby incorporated by reference.

The preparation of monoclonal antibodies likewise is conventional. See, for example, Kohler & Milstein, 1975, *Nature* 256:495; Coligan et al., sections 2.5.1–2.6.7; and Harlow et al, in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose size-exclusion chromatography, and ion-exchange chromatography. See, e.g., Coligan et al sections 2.7.1–2.7.12 and sections 2.9.1–2.9.3; Barnes et al., "Purification of Immunoglobulin G (IgG)," in: *Methods in Molecular Biology*, Vol. 10, pages 79–104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and: allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al, 1990, *Int. J. Cancer* 46:310, which are hereby incorporated by reference.

Alternatively, a therapeutically useful anti-mycothiol or anti-mycothiol precursor antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al. 1989, *Proc. Nat'l Acad. Sci. USA* 86:3 833, which is hereby incorporated in its entirety by reference. Techniques for producing humanized monoclonal antibodies are described, for example, by Jones et al 1986, *Nature* 321:522; Riechmann et al., 1988, *Nature* 332:323; Verhoeyen et al., 1988, *Science* 239:1534; Carter et al., 1992, *Proc. Nat'l Acad. Sci. USA* 89:4285; Sandhu, 1992, *Crit. Rev. Biotech.* 12:437; and Singer et al., 1993, *J. Immunol.* 150:2844, which are hereby incorporated by reference.

Antibodies of the invention also may be derived from antibody fragments isolated from a combinatorial immunoglobulin library. See, for example, Barbas et al, 1991, in: *Methods; a Companion to Methods in Enzymology*, Vol. 2, page 119; Winter et al, 1994, *Ann. Rev. Immunol.* 12:433, which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al, 1994, *Nature Genet.* 7:13; Lonberg et al., 1994, *Nature* 368:856; and Taylor et al., 1994, *Int. Immunol.* 6:579, which are hereby incorporated by reference.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, 1988, *Antibodies: A Laboratory Manual*, Cold Spring Harbor Laboratory, New York, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoff et al., 1960, *Arch. Biochem. Biophys.* 89:230; Porter, 1959, *Biochem. J.* 73:119; Edelman et al., 1967, *Methods in Enzymology*, Vol. 1, page 422, Academic Press; and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al, 1972, *Proc. Nat'l Acad Sci USA* 69:2659. Alternatively, the variable chains can be linked by an intermolecular disulfide bond or crosslinked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., 1991, *Methods: a Companion to Methods in Enzymology*. Vol. 2, page 97; Bird et al., 1988, *Science* 242:423–426; Ladner et al., U.S. Pat. No. 4,946,778; Pack et al., 1993, *Bio/Technology* 11:1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al, 1991, *Methods: a Companion to Methods in Enzymology*, Vol. 2, page 106.

Antibodies which bind to mycothiol or precursor thereof can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. "Purified antibody" refers to that which is sufficiently free of other proteins, carbohydrates, and lipids with which it is naturally associated. Such an antibody "preferentially binds" to mycothiol or a precursor thereof, and does not substantially recognize or bind to other antigenetically unrelated molecules. By "binds specifically" is meant high avidity and/or high affinity binding of an antibody to a specific molecule, e.g., mycothiol or a precursor thereof. Antibody binding to its epitope on a specific molecule is preferably stronger than binding of the same antibody to any other molecule, particularly those which may be present in molecules in association with, or in the same sample. Those of skill in the art will know of various techniques common in the immunology arts for purification and/or concentration of polyclonal antibodies, as well as monoclonal antibodies (See for example, Coligan et al. Unit 9, *Current Protocols in Immunology*. Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

By "labeled antibody," "detectably labeled antibody"" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds., 1988, *Antibodies: A Laboratory Manual*, Cold Spring Harbor Laboratory Press, Cold Spring Harbor, N.Y.).

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Chemical Reagents to Detect Mycothiol Amine Precursors

A reagent that detects mycothiol or its precursor may be a chemical reagent. In one embodiment, the chemical reagent is a reagent which specifically reacts with amines to produce reaction products that are detectable by their emission spectra. One specific, non-limiting example of a reagent that specifically reacts with amines is a reagent for fluorescent amine labeling. A reagent for fluorescent amine labeling is a precolumn derivatization reagent that yields detectable fluorescent adducts. Examples of reagents include dansyl chloride, fluorescamine, 12-(N-methyl-N(7-nitro-2-oxa-1,3-diazol-4-yl) chloride, and CBQCA (Molecular Probes). In one embodiment, the chemical reagent is 6-aminoquinolyl-N-hydroxysuccinimidyl carbamate (AccQ-Fluor) (Cohen, S. and Michaud, M., Analytical Biochemistry. 211,279–287, 1993; Cohen, S. and Michaud, M., 1993, *Techniques in Protein Chemistry IV*, 289–298, herein incorporated by reference). For labeling of amino sugars, a buffer of lower pH than employed with amino acids is utilized. The lower pH provides an advantage to the amino sugars, whose ammonium forms have lower $pK_2$ values than most amino acids, and thus have a competitive advantage during labeling.

The reaction products are then detected. Detection can include any physical or chemical method of detection and or/separation. In the case of change of hydrophilic or hydrophobic properties, there can be used normal phase or reversed phase chromatography. When the molecular weight changes largely, the gel filtration chromatography can be utilized. When the modification of ionic groups or demodification takes place, there can be used ion exchange chromatography. When the sugar chain is added or released, affinity chromatography can be utilized. When the reagent that detects mycothiol is a reagent for fluorescent amine labelling, the fluorescence amine spectra of the reaction products can be utilized. The reaction products can also be quantitated. In one embodiment, high performance liquid chromatography is used for separation and measurement of the reaction products. The AccQ-Fluor derivatized samples were analyzed by HPLC utilizing a Waters 600E solvent delivery system equipped with a Waters WISP Model 710B autoinjector, LDC Fluorometer III, and a Nelson Model 444 data collection system. Separation was obtained on a Beckman Ultrasphere IP (250×4.6 mm) analytical column equipped with a Brownley HPLC guard column containing an OD-GU 5 mm C-18 cartridge using the following linear gradients: 0 min, 100% A (0.1% TFA in water), 10 min, 100% A; 50 min. 60% B (0.1% TFA in methanol); 53 min, 100% B; 57 min, 100% B: 60 min. 100% A; 70 min, reinjection. The flow rate was 1 ml min-1 and the effluent was monitored by fluorescence with a 254 nm excitation filter and a 370–700 nm emission filter. Quantitative determination can further be conducted by any method known to one of skill in the art, such as a fluorescence method or an ultraviolet detection method.

Chemical Reagents to Detect Mycothiol and its Thiol Precursors

A regent that detects mycothiol or precursor may be a chemical reagent. In one embodiment, the chemical reagent is a reagent which specifically reacts with thiols to produce reaction products that are detectable by their emission spectra. One specific, non-limiting example of a reagent that specifically reacts with thiols is a reagent for fluorescent thiol labeling. A reagent for fluorescent thiol labeling is a precolumn derivatization reagent that yields detectable fluorescent adducts. Examples of such reagents include 4-bromomethyl-3,6,7-trimethyl-1,5-diazabicyclo[3.3.0] octa-3,6-diene-2,8-dione (monobromobimane, mBBr) (Kosower, N. S. and Kosower, E. M., 1987, Methods Enzymology, 143:76–84) and 7-diethylamino-3-(4'-maleimidylphenyl)-4-methylcoumarine (CPM) (Molecular Probes).

The reaction products are then detected. Detection can include any physical or chemical method of detection and/or separation. In the case o hydrophilic or hydrophobic properties, there can be used normal or reversed-phase chromatography. When the molecular weight changes largely, gel-filtration chromatography can be utilized. When the modification of ionic groups or demodification takes place, there can be used ion-exchange chromatography. When a sugar chair is added or released, affinity chromatography can be utilized. When the reagent that detect mycothiol is a reagent for fluorescent thiol labeling, the fluorescence spectra of the reaction products can be utilized. The reaction products can also be quantitated. In one embodiment, high performance liquid chromatography is used for separation and measurement of the reaction products (Fahey, R. C. and Newton, G. L, 1987, *Methods Enzymology*, 143:85–96). Quantitative determination can further be conducted by any method known to one of skill in the art, such as fluorescence method or an ultraviolet detection method.

Detection of an Actinomycetes-associated Disorder

The reagent that detects mycothiol or precursor thereof of the invention can be used to detect an actinomycetes-associated disorder. The method includes contacting a sample from a subject having or at risk of having an actinomycetes-associated disorder with a reagent that detects mycothiol or precursor thereof, and detecting the reaction of the reagent. The reaction of the reagent with the sample is then compared to a control. The term "actinomycetes-associated disorder" denotes any disease associated with the presence of actinomycetes such as mycobacteria. An example of an actinomycetes-associated disorder is tuberculosis, which is associated with an infection of *M. tuberculosis*. Any biological sample which may contain a detectable amount of mycothiol or precursor thereof can be used. Examples of biological samples of use with the invention are blood, serum, plasma, urine, mucous, feces, cerebrospinal fluid, pleural fluid, ascites, and sputum samples. Tissue or cell samples can also be used with the subject invention. These samples can be obtained by many methods such as cellular aspiration, or by surgical removal of a biopsy sample. The level of mycothiol or a precursor thereof in the sample can be compared with the level in a sample not affected by the disease process. The sample not affected by the disease process can be taken from the same subject, or can be from a control subject not affected by the disease process, or can be from a cell line. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Those of skill in the art will know, or can readily discern, an appropriate immunoassay format without undue experimentation.

The antibodies of the invention can be bound to many different carriers, both soluble and insoluble, and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. Those skilled in the art will know of other suitable carriers for binding antibodies, or will be able to ascertain such, using routine experimentation. In addition, there are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds, as described above.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The monoclonal antibodies or polynucleotides of the invention can be used in vitro and in vivo to monitor the course of amelioration of an actinomycetes-associated disease in a subject. Thus, for example, by measuring the increase or decrease in the number of cells expressing antigen comprising a polypeptide of the invention or changes in the concentration of such antigen present on cells or in various body fluids, it would be possible to determine whether a particular therapeutic regimen, such as an antibiotic regimen, aimed at ameliorating the actinomycetes-associated disease is effective. The term "ameliorate" denotes a lessening of the detrimental effect of the actinomycetes-associated disease in the subject receiving therapy.

This invention involves administering to a subject a therapeutically effective dose of a pharmaceutical composition containing the antibodies of the present invention and a pharmaceutically acceptable carrier. "Administering" the pharmaceutical composition of the present invention may be accomplished by any mears known to the skilled artisan. By "subject" is meant any mammal preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, 1990, *Science* 249:1527–1533, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990, each of which is herein incorporated by reference.

Thus the availabilities of reagents that detect actinomycetes provides a useful tool for diagnosis, prognosis and therapeutic strategies.

Identification of Samples with Altered Production of Mycothiol

The invention provides a method for identifying samples with altered production of mycothiol or a precursor thereof. A "test sample" is any sample to be evaluated for the production of mycothiol or precursor thereof. In one embodiment, the sample is an isolated sample of actinomycetes, such as a mycobacteria sample. In another embodiment, the sample is a biological sample with a known actinomycetes infection. Such samples may be identified by conventional methods of detecting actinomycetes, such as by histological staining or by moleuclar methods such as polymerase chain reaction. The method of the invention can be used in order to determine if the actinomycetes has altered production of mycothiol or a precursor thereof. As only viable actinomycetes produce mycothiol and its thiol precursors in the reduced thiol form, the method of the invention can futher be used to determine if the actinomycetes are viable.

The test sample is contacted with a reagent that detects mycothiol or precursor thereof for a period of time sufficient for the reagent to react with mycothiol or precursor thereof. The reaction of the reagent is then detected and compared to the reaction of the reagent with a control. One of skill in the art can readily determine an appropriate control sample. In a specific non-limiting example, the control sample can be any sample which has a defined level of production of mycothiol or precursor thereof. In another specific non-limiting example, the control is a known concentration of partially purified or purified mycothiol or precusor thereof. In yet another specific non-limiting example, the control is generated as a standard curve.

The production of mycothiol in the sample may be increased as compared to the control. In one embodiment, mycothiol or a precursor thereof is substantially increased above the defined reference level greater than or equal to a 20% increase, preferably greater than or equal to a 50% increase, more preferably greater than or equal to a 75% increase, with the most preferred being a 100% increase above the control. In another embodiment, mycothiol or a precursor thereof is substantially decreased below the defined reference level greater than or equal to a 20% decrease, preferably greater than or equal to a 50% decrease, more preferably greater than or equal to a 75% decrease, with the most preferred being a 100% decrease below the control.

The control sample can be any sample that produces a reference standard of mycothiol or precursor thereof. In one embodiment, the control is a sample of actinomycetes known to produce mycothiol or precursor thereof. In another embodiment, the control may be a biological fluid or sample, known to be free of actinomycetes, into which a known quantity of actinomycetes is introduced. Alternatively, known amounts of purified mycothiol or a precursor thereof may be used as a control. One of skill in the art will readily be able to identify suitable controls for use with the method of the invention.

Bacterial Identification

Mycothiol production is specific to the taxa actinomycetes. Thus in order to idenify if an organism of interest is a member of the taxa actinomycetes, an assay may be used to assay for the presence or absense of mycothiol or a precursor thereof. The organism may be obtained from any sample of interest, and in particular may be cultured from a patient sample of interest, such as a blood sample, a serum sample, a urine sample, a fecal sample, a tissue biopsy, cerebrospinal fluid sample, ascites sample, pleural fluid sample, respiratory secretions including broncial secretion samples obtained by bronchoscopy and a sputum sample. One of skill in the art will readily be able to determine culture conditions, either in liquid or on a solid medium, for a bacterium of interest (Manual of Clinical Microbiology, 6th Edition (Murray, P. Editor in Chief) American Society for Microbiology Press, Washington, D.C. 1995). In one embodiment, the bacterial culture is "clonal" or derived from one cell. In another embodiment, the bacterial culture is a mixed population containing two or more different organisms or strains.

The method includes contacting a membrane to a bacteria plated on a bacterial culture plate for a time sufficient to allow the bacteria to adhere to the membrane. Several membranes are known to one of skill in the art for the adhesion of bacteria. Specific non-limiting examples of these membranes include nitrocellulose (Nitropure) or other membranes used in for detection of bacterial gene expression including polyvinylchloride, diazotized paper and other commercially available membranes such as Genescreen. The adherent bacteria are then lysed by any method known to one of skill in the art. A specific, non-limiting example of a method to lyse bacteria is N-acetylglucosaminidase (3.1 units in 10 ml TBS adjusted to pH 4.2 with acetic acid). However, other methods of bacterial lysis, such as treatment with lysozyme or sonication are well known to one of skill in the art and can also be utilized (see Sambrook et al, *Molecular Cloning: a Laboratory Manual*, Cold Spring Harbor Press, 1989, the contents of which are incorporated by reference).

The membrane is contacted with a reagent to detect mycothiol or a precursor thereof, and the reaction of the reagent with mycothiol or a precursor thereof is detected. In one embodiment, the reagent is an antibody, such as a polyclonal antibody which specifically binds mycothiol or a precursor thereof. The antibody can be directly labeled, or a suitable detection scheme can be utilized. In one embodiment, a labeled secondary antibody which binds to the antibody which binds to mycothiol or a precursor thereof can be can be utilized. Labels for antibodies have been described above. Many such detection schemes for an antibody are well known to one of skill in the art (see Harlow, E. and Lane, D., Antiboides: A. Laboratory Mannual, Cold Spring Harbor Press, 1988, the contents of which are herein incorporated by reference).

The materials for use in the assay of the invention are ideally suited for the preparation of a kit. Such a kit may comprise a carrier means containing one or more container means such as vials, tubes and the like each of the container means comprising one of the separate elements to be used in the method. One of the container means may comprise a reagent to detect mycothiol or precursor thereof. In one embodiment, the reagent is an antibody that specifically binds to mycothiol or a precursor thereof. The kit may also contain a container comprising detection means, such as a container containing a detection reagent to detect the reaction of mycothiol or precursor thereof with said reagent to detect mycothiol or precursor thereof. For example, the reagents for detecting mycothiol or a precursor thereof of the present invention can be included in a kit and used for examining the presence of a actinomycetes in a sample. The sample may be a patient sample, such as a blood sample, a serum sample, a urine sample, a fecal sample, a tissue biopsy, cerebrospinal fluid sample, ascites sample, pleural fluid sample, respiratory secretions, including broncial secretion samples obtained by bronchoscopy and a sputum sample. The sample can also be a bacterial sample, either a mixed population or a clonal sample.

Where the kit utilizes antibodies to detect mycothiol or a precursor thereof, these antibodies may be directly labeled. The kit may also contain a container containing a reporter means, such as avidin or streptavidin, bound to a reporter molecule such as an enzymatic, fluorescent, or radionucleotide label to identify the directly labeled antibody. Alternatively, the kit can utilize antibodies that bind mycothiol or a precursor thereof that are unlabeled. The kit may then also contain a container containing a second antibody which binds to the antibody specific for mycothiol or a precursor thereof. The second antibody can be directly labeled. The kit may further include a container containing a reporter means, such as avidin or streptavidin, bound to a reporter molecule such as an enzymatic, fluorescent, or radionucleotide label to identify the second antibody.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

List of Abbreviations for Mycothiol and its Precursors and their Chemical Adducts 1. Formal name: 1-D-myo-inosityl-2-(N-acetyl-L-cysteinyl)amido-2-deoxy-α-D-glucopyranoside. Trivial name "mycothiol". Abbreviated "MSH" or "AcCys-GkcN-Ins".

2. Formal name: 1-D-myo-inosityl-2-(L-cysteinyl)amido-2-deoxy-α-D-glucopyranoside. Abbreviated "Cys-GlcN-Ins".

3. Formal name: 2-D-myo-inosityl-2-amino-2-deoxy-α-D-glucopyranoside. Abbreviated "GlcN-Ins".

4. Formal name: 2-(N-acetyl-L-cysteinyl)amido-2-deoxy-α-d-glucopyranoside. Abbreviated "AcCys-GlcN".

5. Formal name: 2-(L-cysteinyl)amido-2-deoxy-α-D-glucopyranoside. Abbreviated "Cys-GlcN".

6. Compounds prefixed by "AccQ-" indicate the AccQ-Fluor derivative of that compound. Thus, "AccQ-GlcN-Ins" indicates the AccQ-Fluor derivative of 1-D-myo-inosityl-2-amino-2-deoxy-α-D-glucopyranoside.

7. Compounds prefixed by "mB-" indicate the monobromobimane derivative of that compound. Thus, "mB-Cys-GlcN" indicates the monobromobimane derivative of 2-(L-cysteinyl)amido-2-deoxy-α-D-glucopyranoside.

Example 1

Mycothiol Purification
Materials and Organisms

*Mycobacterium smegmatis*—mc$^2$6 and mc$^2$155 were provided by J. Davies (University of British Columbia, Vancouver, British Columbia). Carrier proteins (bovine serum albumin, ovalbumin, and keyhole limpet hemocyanin, and maleimide-activated bovine serum albumin), crosslinking reagents (maleimidobenzoyl-N-hydroxysulfosuccinimide ester, N-succinimidyl-3-(2pyridyldithio)propionate), and desalting columns (KwikSep crosslinked dextran) were purchased from Pierce. Epoxy-activated Sepharose 6B was obtained from Pharmacia. Nitrocellulose membrane (0.4 μm porosity) and Tween-20 were purchased from BioRad. NitroPure supported nitrocellulose membranes (81 mm diameter circles, 0.45 μm porosity) were purchased from MSI. 96-Well microtitre plates (Immulon-4) were purchased from Dynatech. Goat anti-rabbit-IgG (whole molecule) secondary antibody (F(ab')$_2$ fragments conjugated to bovine intestinal alkaline phosphatase), fish-skin gelatin, N-acetylglucosaminidase (from jack beans), L-cysteine hydrochloride, N-acetyl-L-cysteine, coenzyme A (sodium salt), glucosamine hydrochloride, glutathione, and pantethine were purchased from Sigma Chemical Co., as were the alkaline phosphatase substrates 5-bromo-4-chloro-3-indolyl phosphate/nitroblue tetrazolium ("SigmaFAST" BCIP/NBT) and p-nitrophenyl phosphate. Manobromobimane was obtained from Molecular Probes, Inc. High-purity, heavy-metal-free dithiothreitol (DTT) was obtained from Calbiochem. S-Trityl-cysteine, S-trityl-N-Boc-cysteine, and 2-(5-norbornene-2,3-dicarboximido)1,1,3,3-tetramethyluronium tetrafluoroborate were from Calbiochem-Novabiochem, and diisopropylethylamine from Pierce. S-Trityl-N-acetyl-cysteine was prepared by the general procedure given by Stewart and Young (Stewart, J. M., and Young, J. D., 1984, "Solid Phase Peptide Synthesis," Pierce Chemical Co., Rockford, Ill.).

Pantetheine was prepared by DTT reduction of pantethine: 3 μmol pantethine was dissolved in 30 μl ultrapure water, and a solution of 22 μmol dithiothreitol in 220 μl ultrapure water was added. The mixture was allowed to react for 15 minutes at room temperature, after which the solution was acidified to pH ~1 by the addition of 10 μl of 5 M methanesulfonic acid. Residual dithiothreitol was removed by trituration of the reaction mixture with eight portions of water-saturated ethyl acetate (250 μl each). The aqueous phase was stored frozen until use. Immediately before use, the pantetheine content was determined by titration with DTNB (Ellman, G. L., 1959, *Arch. Biochem. Biophys.* 82:70).

All other reagents were reagent grade or higher purity.

2-(Cysieinyl)amido-2-deoxy-α/β-D-glucopyranose (CysGlcN) and 2-(N-acetylcysteinyl)amido-2-deoxy-α/β-D-glucopyranose (AcCysGlcN)

S-trityl-N-acetyl-cysteine or S-trityl-N-Boc-cysteine (1 mmol) and 2-(5-norborene-2,3dicarboximido)-1,1,3,3-tetramethyluronium tetrafluoroborate (1.1 mmol) were dissolved in dimethylformamide (1 ml) with diisopropylethylamine (0.26 ml) and stirred at room temperature for 15 min. This mixture was then added drop-wise to a stirred solution of glucosamine hydrochloride (0.6 mmol) in 12 ml 0.25 M imidazole HCl (pH 7.0, 50% acetonitrile) and allowed to react for 1 h at room temperature before acidifying with trifluoroacetic acid. The product was purified by reversed-phase HPLC on a Vydac C18 column eluted with a linear gradient (40–100% aqueous acetonitrile containing 0.1% trifluoroacetic acid) and dried under reduced pressure. Typical yields were 40–60%. The Boc and/or trityl protecting groups were removed using trifluoroacetic acid containing DTT which was then diluted into water before extracting with ethyl acetate (1 vol., 10 times) to remove scavenger. The resulting free thiol was quantified by titration with Ellman's reagent, 5,5'-dithiobis(2-nitrobenzoic acid) (DTNB) (Ellman, 1959, supra) and was characterized as the monobromobimane derivative to be an approximately 1:2 mixture of α to β epimers by HPLC (Newton et al, 1995, supra).

*Mycobacterium smegmatis* mc²6 was grown to early stationary phase in Middlebrook 7H9 medium supplemented with 0.5% w/v Tween-80 and 0.4% w/v glucose. MSH content was determined by HPLC analysis of the monobromobimane-labeled derivative (Newton et al., 1995, supra).

Crude MSH was isolated from stationary-phase cultures according to the general method of Newton & Fahey (Newton, G. L., and Fahey, R. C., 1987, *Methods Enzymol.*, 143:96). The cultures were centrifuged to pellet the cells and the supernatant discarded. The pelleted cells (297 g wet weight) were lysed by homogenization in 2.0 l warm (60° C.) 50% v/v aqueous acetonitrile containing 25 mM methanesulfonic acid, followed by 15 minutes incubation at 60° C. During subsequent steps, extracts were kept chilled on ice. Cellular debris was removed by centrifugation, then the acetonitrile was removed by rotary evaporation from the supernatant. Dithiothreitol was added to the remaining aqueous suspension and solid tris(hydroxymethyl)aminomethane (Tris) base added with stirring until the pH reached 8.0. Precipitates were again removed by centrifugation and the clear supernatant loaded on a thiol-affinity column (thiopropyl Sepharose 6B activated with thiopyridyl, 25 mm×90 mm). After rinsing the column with 1.01 50 mM Tris, pH 8, and 500 ml 50 mM ammonium bicarbonate buffer, pH 8, the bound mycothiol was eluted off the column with 300 ml 20 mM DTT in ammonium bicarbonate buffer, pH 8.

The crude extract was purified by reversed-phase HPLC on a preparative C 18 column, 25 mm×250 mm (Vydac) by isocratic elution with 0.1% trifluoroacetic acid (TFA) in ultrapure water at a flow rate of 10 ml/min. Under these conditions MSH eluted as the free thiol at 8 minutes and as its disulfide (MSSM) at 12 minutes. Thiol concentration was determined by titration with DTNB. Purified MSH was stored as a concentrated (0.11 M) stock solution in 0.1% TFA (aqueous), frozen at −70° C. Under these conditions MSH was stable as the free thiol for many months.

Example 2

Preparation of Mycothiol-carrier Protein Conjugates

In designing an antigen, mycothiol is to be crosslinked by its sulfhydryl functionality to the carrier proteins in order to maximize surface presentation of mycothiol's novel disaccharide moiety, as well as to take advantage of the specific reactivity of the sulfhydryl group. We used two carrier proteins for antigen preparation: bovine serum albumin (BSA) and keyhole limpet hemocyanin (KLH). In addition to the more commonly used BSA, we chose KLH, a large multimeric protein, for its generally high antigenicity in vertebrates. The crosslinking reagent used, sulfo-MBS, efficiently reacts with lysine amino groups in carrier proteins via its succinimide functionality and then with sulfhydryl-containing compounds via its maleimide functionality (Equation 1).

Equation 1

Protein—NH₂ + sulfo-MBS —MSH→

(BSA or KLH)

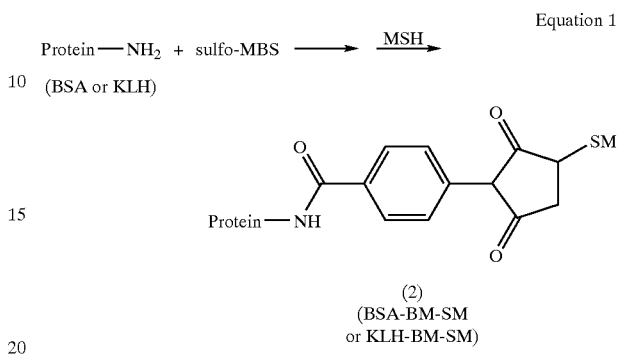

(2)
(BSA-BM-SM or KLH-BM-SM)

Purified MSH from *Mycobacterium smegmatis* was conjugated to keyhole limpet hemocyanin (KLH) by treatment with the bifunctional crosslinking reagent, maleimidobenzoyl-N-hydroxysulfosuccinimide ester (sulfo-MBS). The sulfo-MBS was first reacted with KLH, and then the MBS-activated KLH reacted with MSH at both a low and a high degree of coverage. HPLC analysis of the monobromobimane-labelled residual MSH showed good yields from the crosslinking reactions estimated to be ~90–100% (low-coverage conjugates) and ~85% (high-coverage conjugates).

A typical procedure follows: 4 mg KLH was dissolved in 400 μl phosphate-buffered saline (PBS), pH 7.2, with 0.1 M ethylenediaminetetraacetic acid added ("conjugation buffer"). A solution of 0.4 mg sulfo-MBS in 200 μl conjugation buffer was added to the KLH and the mixture reacted for 1 h at room temperature The reaction mixture was then passed through a desalting column (Pierce KwikSep, 5 ml bed volume) to remove excess sulfo-MBS. Eluted fractions were monitored at 280 nm and the protein-containing fractions combined. The sulfo-MBS-activated KLH was divided into two equal aliquots (each containing 2 mg activated KLH in 1100 μl). Purified MSH (either 0.303 μmol or 1.212 μmol MSH) was added to 100 μl conjugation buffer and this solution was added to the KLH suspensions. The mixtures were reacted for 2 h at room temperature and then concentrated to ~400 μl by centrifugation on Centricon ultrafilters, 2 h at 770×g at 4° C. The conjugates were stored in ~500 μg aliquots, frozen at −20° C. The efficiency of crosslinking was determined by HPLC analysis of the monobromobimane-labeled residual MSH from the Centricon filtrates.

Sera from rabbits immunized with KLH-BM-SM were pooled and the MSH-specific antibodies purified by affinity chromatography. We chose epoxy-activated Sepharose 6B as the affinity chromatography medium in order to covalently immobilize MSH via its sulfhydryl group (Equation 2).

Equation 2

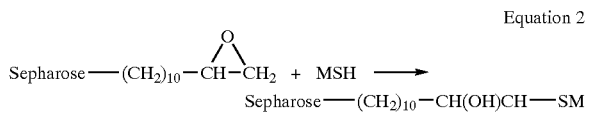

The linker arm on this material is 12 atoms long, permitting a flexible presentation of the antigen to the antibodies. It is structurally distinct from the linker used in preparing the antigen (Equation 1) and was therefore expected to have lower affinity for antibodies directed to the antigen linker region. The chromatography was monitored by dot-blots; the purified MSH-specific antibody fractions were pooled, concentrated, and stored frozen in aliquots.

The affinity resin was prepared as follows: 1 g epoxy-activated Sepharose 6B (Pharmacia) was suspended in 200 ml ultrapure water, fined, transferred to a sintered glass funnel, and washed under mild vacuum with 100 ml 0.1 M carbonate buffer, pH 8.5, to give 3 ml swelled gel which was transferred to a conical tube. Pure MSH (40 μmol) in 364 μl 0.1% TFA (aqueous) was added to 364 μl 0.1 M carbonate buffer and the pH of the mixture adjusted to 8.5. This was immediately added to 3 ml Sepharose, the suspension was mixed vigorously and incubated for 22 h at room temperature on a rotating mixer. The gel was then transferred to a sintered glass funnel, rinsed with 30 ml carbonate buffer, and transferred back to a conical tube. Determination of the unbound MSH that remained showed that a total of 35 μmol had reacted, corresponding to approximately one-third of the available epoxy groups. The remaining epoxy groups were blocked by reaction with 7 ml of 1 M ethanolamine, pH 9.5, for 4 h at room temperature The MSH-Sepharose was then rinsed on a sintered glass funnel with alternate 30 ml rinses (3 each) of 0.1 M acetate buffer, pH 4.0 and 0.1 M carbonate buffer, pH 8.3 (each containing 0.5 M NaCl). Finally, the MSH-Sepharose gel was washed with 100 ml PBS, pH 7.2, 0.04% $NaN_3$, and stored at 4° C.

A typical affinity-purification follows: 3 ml MSH-Sepharose was slurry-packed with PBS in a 10 mm-i. d. column, degassed, and allowed to settle to give a bed height of ~40 mm. All of the following steps were carried out at 4° C. The column was washed sequentially with 30 ml each of: 10 mM Tris, pH 7.5; 100 mM glycine, pH 2.5; 10 mM Tris, pH 8.8; and 100 mM triethylamine, pH 11.5. The column was then rinsed with 60 ml PBS. The ammonium sulfate IgG fractions (~15 ml) were thawed and passed through the column four times at 15 ml/h. Unbound serum was saved for dot blot analysis. Next, the column was washed with 60 ml of 10 mM Tris, pH 7.5, followed by 60 ml of 10 mM Tris, pH 7.5, 0.5 M NaCl. MSH-specific IgG's were eluted with both low-pH (100 mM glycine, pH 2.5) and high-pH (100 mM triethylamine, pH 11.5) buffers. Eluted fractions were analyzed by dot blots for MSH-specific IgG; fractions containing the purified antibodies were combined, dialyzed against PBS/0.04% $NaN_3$, and stored frozen in aliquots at −20° C.

The following presents an exemplary but not exhaustive list of reagents that may be used to bind mycothiol to a carrier protein for the purpose of raising antibodies. Sulfo-MBS was used for this purpose. The following is a list of possible substitute reagents. The "Sulfo-" reagents are more water soluble than the parent reagents, but have the same chemistry. The following comes from the Pierce Chemical catalog which is a common source for such reagents.

| Abbreviation | Chemical Name |
| --- | --- |
| APDP | N-[14-(p-azidosalicylamido)butyl]-3-(2'pyridyldithio)propionamide |
| GMBS | N(γ-maleimidobutyrloxy)succinimide ester |
| MBS | M-maleimidobenzoyl-N-hydroxysuccinimide |
| SIAB | N-succinimidyl(4-iodoacetyl)aminobenzoate |
| SMCC | Succinimidyl4-(N-maleimidomethyl)-cyclohexane-1-carboxylate |

-continued

| Abbreviation | Chemical Name |
| --- | --- |
| SMPB | Succinimidyl4-(p-maleimidophenyl)-butyrate |
| SPDP | N-succinimidyl-3-(2-pyridyldithio)proprionate |
| Sulfo-GMBS | N(γ-maleimidobutyryloxy)sulfo-succinimide ester |
| Sulfo-MBS | m-maleimidobenzoyl-N-jydroxysulfo-succinimide |
| Sulfo-SIAB | Sulfosuccinimidyl4-(N-maleimidomethyl)-cyclohexane-1-carboxylate |
| sulfo-SMPB | Sulfosuccinimidyl4-(p-maleimidophenyl)-butyrate |

The following reagents are examples that could be used to link mycothiol to ovalbumin for use in the dot blot assays described above to identify fractions of IgG that contain MSH antibodies elicited by KLH-M-SM. SPDP was used in the studies described.

| | |
| --- | --- |
| SPDP | N-succinimidyl-3-(2-pyridyldithio)proprionate |
| APDP | N-[4-(p-Azidosalicylamido)butyl]-3'-(2'-pyridyldithio)propionamide |
| LC-SPDP | Succinimidyl 6-[3-(2-pyridylithio)-propionamido]hexanoate |
| Sulfo-LC SPDP | Sulfosuccinimidyl 6-[3-(2-pyridyldithio)-propionamido]hexanoate |
| Sulfo-SADP | Sulfosuccinimidyl(4-azidophenyldithio)-propionate |
| Sulfo-LC-SMPT | Sulfosuccinimidyl 4-(p-maleimidophenyl)-butyrate |

Example 3

Polyclonal Antibody Preparation

Antibodies were raised in female New Zealand rabbits by immunization with the KLH-BS-SM conjugates. After pre-immune serum samples were taken, the rabbits were immunized with 500 μg of conjugate in 500 μl PBS plus 500 μl Freund's complete adjuvant. The rabbits received a second immunization (identical to the initial immunization) after three weeks. Subsequent immunizations consisted of conjugate plus Freund's incomplete adjuvant. Blood samples were taken from the rabbits three weeks after the second immunization and ten to fourteen days after each subsequent immunization.

IgG fractions from rabbit sera were isolated by ammonium sulfate precipitation in two steps (33% and 50% saturation), followed by dialysis against PBS. IgG fractions were stored frozen at −20° C. Each IgG ammonium sulfate preparation was tested for the presence of MSH-specific antibodies by dot blots on nitrocellulose membranes. The BioDot (BioRad) apparatus was used in most cases. Generally, the Tris-buffered saline (TBS, pH 7.3) pre-moistened nitrocellulose membrane was assembled in the apparatus and the test antigens (0. 1 to 1 μg/well) applied to the wells. The membrane was blocked with 200 μl /well 1% fish skin gelatin in TBS before application of the sera. After washing unbound material through the membrane with Tris-buffered saline containing 0.05% v/v Tween-20 (TBST), 100 μl/well of the secondary antibody (goat anti-rabbit-IgG F(ab')$_2$-alkaline phosphatase, 1:30,000 in TBS) were added. Unbound secondary antibody was washed through the membrane with TBST. The entire membrane was then removed from the apparatus, washed with TBS, and covered with a solution of alkaline phosphatase substrate ("SigmaFAST" BCIP/NBT). After spots appeared (typically in 1–2 minutes), the membrane was washed in distilled water and air-dried.

Specificity for MSH and not for the crosslinker (MBS) or carrier protein (KLH) was detected by a positive reaction to MSH conjugated to ovalbumin (OVA) via the non-homologous crosslinking agent N-succinimidyl-3-(2-pyridyldithio)proprionate (SPDP) (OVA-PS-SM, Equation 3).

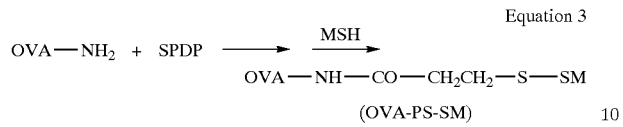

Equation 3

Undiluted sera from the KLH-BM-SM-immunized rabbits detected the lowest amount of antigen (0.1 μg/well of OVA-PS-SM) used in the dot blots. Specific antibodies were detected in the sera after the second immunization, and remained detectable in subsequent boost-bleed cycles.

Sera from rabbits immunized with BSA-BM-SM was also tested by dot blots (using KLH-PS-SM as the test antigen to determine MSH-specificity). Although some specific antibody production was observed, these conjugates did not elicit as strong a response in rabbits as did the KLH-BM-SM conjugates, and the sera from these rabbits was not used.

Example 4

Immobilization of Mycothiol Via its Thiol Funcitonality in the Assay of Mycothiol In any immunoassay, the molecule to be detected must be immobilized and subsequently detected. In the case of mycothiol, there are two general methods for accomplishing these steps. In the first general method, mycothiol is bound via its thiol functionality using thiol-specific chemistry, and subsequently detected by means of an antibody specific to the non-thiol moiety of mycothiol. In the second general method, mycothiol is bound by means of an antibody specific for the non-thiol moiety of mycothiol, and the thiol funtionality subsequently utilized in the detection step (for example, by attaching to the thiol functionality a detectable substance).

The following immunoassay architecture illustrates an example of the first general method.

1. MSH is allowed to react with maleimide-activated bovine serum albumin ("mal-BSA").
2. The MSH-mal-BSA conjugate is allowed to bind by non-specific absorption to a microtiter plate.
3. Anti-MSH antibody is allowed to bind to the immobilized mycothiol.
4. Alkaline phosphatase-labelled goat-anti-rabbit IgG (F(ab')₂ fragments), is allowed to bind to the anti-MSH antibody, and pNPP is used to quantitate the amount of bound alkaline phosphatase. Other reporter enzyme-secondary antibody conjugates may be used.

This immunoassay is depicted in the schematic below:

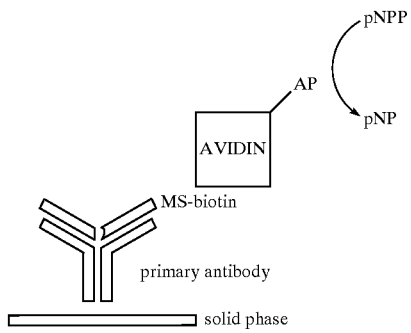

An example of a specific experimental procedure for this type of immunoassay using an ELISA format follows.

Known amounts of pure MSH (typically from 0 to 1 pmol/well) were reacted with maleimide-activated BSA (Pierce); maleimide activation levels were 16–19 mol maleimide per mol BSA. The maleimide-activated BSA was reconstituted to 10 mg/ml and this stock solution stored at −70° C. until needed. The stock solution was diluted to a working concentration of 5 ng/μl just before use and kept chilled on ice. MSH from the concentrated stock solution in 0.1% TFA was diluted into TBS (Tris-buffered saline: 0.1 M Tris, pH 7.3, 0.15 M NaCl, 0.04% NaN$_3$) on ice and the diluted samples (40 μl per well) immediately added to the maleimide-activated BSA (60 μl per well). A "zero" standard consisted of TBS in place of an MSH solution. In practice, 168 μl of thiol standard were added to 252 μl of maleimide-activated BSA solution. Samples of unknown thiol content were reacted with maleimide-activated BSA in the same manner, providing a small excess volume for pipetting of quadruplicate samples of 100 μl per well. After 2-hour incubation at room temperature, the thiol-BSA samples were aliquoted (100 μl per well) into Immulon-4 microplate wells and allowed to bind overnight at 4° C. Unbound protein was removed by gentle aspiration with mild vacuum and the wells blocked for 2 hours at room temperature with 1% v/v fish-skin gelatin in TBS. The wells were drained, washed once with TBST (TBS plus 0.05% Tween-20), and drained. Washes involved filling wells to the top with wash buffer followed by gentle aspiration to drain the wells. Primary antibody (affinity-purified anti-MSH, 100 μl per well) was added and the plate incubated for 4 hours at room temperature. The wells were drained, washed twice with TBST, and drained. Secondary antibody (goat anti-rabbit [whole IgG] F(ab')₂ fragments conjugated to bovine intestinal alkaline phosphatase, 100 μl per well) was added and the plate incubated for 1 hour at room temperature. The wells were drained, washed twice with TBST, twice with TBS, and drained. The alkaline phosphatase substrate (3.8 mM p-nitrophenylphosphate in 0.2 M Tris, pH 9.8, 200 μl per well) was added and the plate incubated 30 minutes at room temperature. The reaction was quenched by addition of 50 μl per well stop solution (4 N NaOH). The plate was read at 405 nm on a microplate reader (Model EL311, Bio-Tek Instruments) that was programmed to automatically subtract blank values read from wells that received only the blocking agent, wash solutions, p-nitrophenyl phosphate, and stop solution. The difference in optical density was calculated for wells that had received known amounts (0.1 to 1.0 pmol per well) of MSH by subtracting from these values the mean optical density of wells that had received the "zero" standard.

Figure 2:
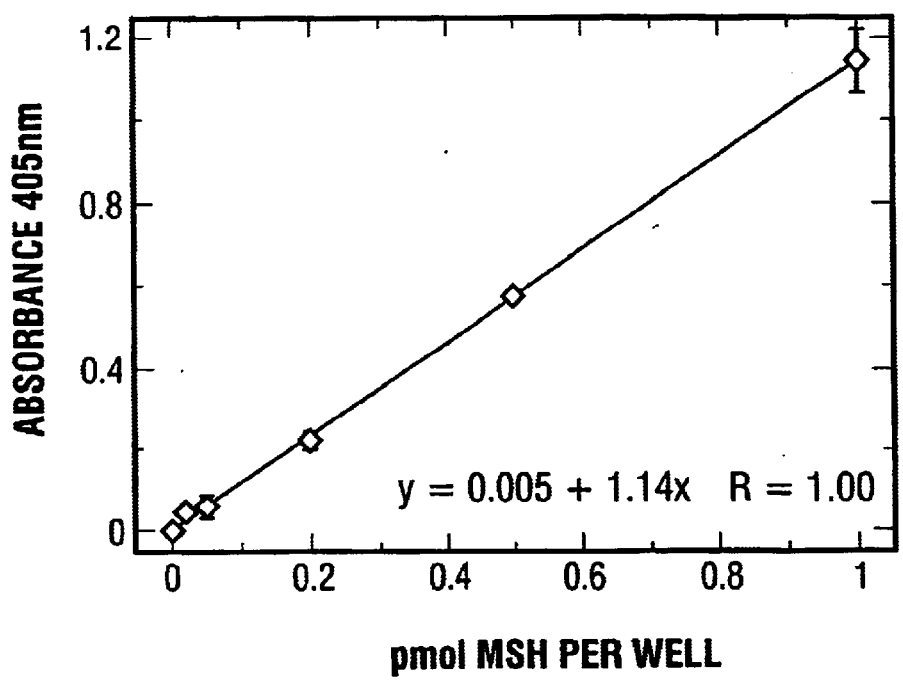
FIG. 2 is a typical standard curve obtained using the ELISA procedure described in Example 4, using purified mycothiol from 0.02–1.0 pmol per well. Samples were run in quadruplicate; error bars indicate standard deviation from the mean.

The ELISA protocol described above was based upon the results of assays in which the amounts of maleimide-activated BSA, primary antibody, secondary antibody, and blocking protein were varied, and upon the testing of different types of secondary antibody, blocking reagent, microtiter plates, washing protocols, and incubation limes. The adopted protocol as described above measures pure MSH in buffer with the sensitivity and linearity illustrated in FIG. 2. This ELISA has a useful range of about 0.1–1 pmol MSH, and a detection limit of at least 0.1 pmol MSH, and thus is approximately an order of magnitude more sensitive than the HPLC assay of monobromobimane-labelled MSH (Newton et al., 1993, *J. Bacteriol.*, 175:2734).

Example 5

Analisis of Mycothiol from Cell Lysates

The immunoassay described in Example 4 was used in the ELISA format to analyzed cell lysates for their mycothiol content. In most experiments, parallel mycothiol determinations were made using HPLC analysis of monobromobimane-labelled cell lysates. A typical procedure follows.

*Mycobacterium smegmatis* mc$^2$6 was grown in Middlebrook 7H9 medium supplemented with 0.4% w/v glucose and 0.05% v/v Tween-80. A conversion factor of $0.25 \times 10^9$ colony-forming units per mL (CFU/mL) per absorbance unit measured at 600 nm was used to determine cell density. Cells used in experiments were harvested at early- to mid-log phase growth. Typically, cells were diluted in phosphate-buffered saline, pH 7.2 (PBS) to a desired cell density. Cell samples were centrifuged 5 min at 12,000×G. Most of the supernatant was removed and discarded, leaving the cell pellet in a volume of about 100 μL. Optionally, a small volume of PBS or Tris-buffered saline (TBS) was added, and the cells resuspended. Acetonitrile was added to a final concentration of 50% v/v, the samples vortexed, and incubated 10 min at 60° C. to lyse the cells. The lysates were centrifuged 45 sec at 12,000×G to pellet cell debris, and an aliquot (40 μL per well) of the supernatant immediately added to a freshly-made solution of maleimide-activated BSA (60 μL per well of a 5 ng/μL solution in TBS). After a 2-hour incubation at room temperature, the reaction mixtures were aliquoted (100 μL per well) into Immulon-4 microtiter plate wells and allowed to bind overnight at 4° C. Standard mycothiol samples were prepared and run as controls on the same plate. Blocking, washing, antibody-binding, and detections steps were identical to those described in Example 4. Cell lysates from the most concentrated cell samples were derivatized with monobromobimane and analysed for their mycothiol content by HPLC as previously described (Newton et al., 1993, *J. Bacteriol.*, 175:2734). The results are summarized in Table 1.

TABLE 1

Determination of MSH in *Mycobacterium smegmatis* by ELISA in comparison to determination by monobromobimane labeling and HPLC analysis

| Method of analysis | CFU analyzed | Volume (μl) analyzed | pmol MSH(n$^a$) | pmol/10$^6$ CFU(n$^a$) |
|---|---|---|---|---|
| HPLC | $4.8 \times 10^6$ | 100 | 67 | 14.0 |
| HPLC | $3.0 \times 10^5$ | 50 | 4 | 13.3 |
| ELISA | $7.7 \times 10^4$ | 40 | 1.02 ± 0.08 (4) | 13.3 ± 1.0 (4) |
| ELISA | $3.9 \times 10^4$ | 40 | 0.40 ± 0.04 (4) | 10.2 ± 1.0 (4) |
| ELISA | $7.7 \times 10^3$ | 40 | 0.073 ± 0.011 (4) | 9.4 ± 1.5 (4) |

$^a$number of determinations (n)

The results obtained by ELISA on the most concentrated samples agreed well with the HPLC results, whereas the ELISA values were 30% lower at the limit of sensitivity. The sensitivity of the HPLC method is limited by the signal-to-noise ratio for fluorescent detection and was about 1 pmol for the present samples, or 10-fold less sensitive than this ELISA protocol. This ELISA protocol requires fewer cells (~$10^4$ cells) than does the HPLC method (~$10^6$ cells) in order to detect a measurable amount of MSH.

Example 6

Figure 3:
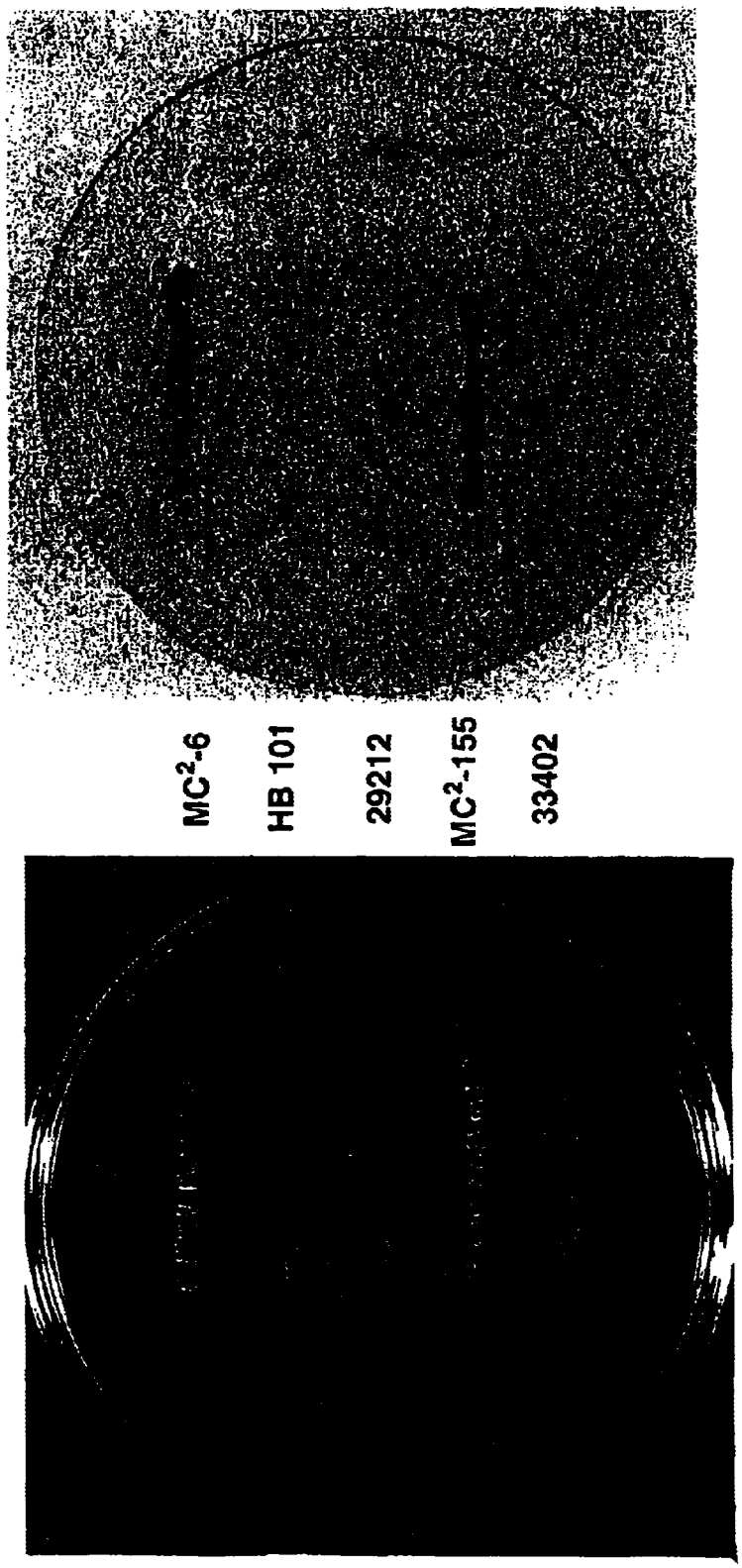
FIG. 3 illustrates membrane blot detection of mycothiol in bacterial colonies lifted from a culture plate: (top to bottom) *Mycobacterium smegmatis* mc$^2$6, *Escherichia coli* HB101, *Enterococcus faecalis* ATCC 29212, *Mycobacterium smegmatis* mc$^2$155, *Streptococcus mutans* ATCC 33402. Left—photograph of colonies; Right—mycothiol determination by dot blot assay.

A Colony-lift Blot Procedure for the Detection of Mycothiol-producing Bacterial Colonies Grown on Solid Media A membrane-based assay based on the immunoassay architecture described in Example 4 was developed for detecting MSH production by bacterial colonies grown on solid media. The following protocol is typical for a single 100 mm Petri dish. All incubations were done at room temperature on an orbital platform shaker set to 90 rpm unless otherwise noted. Different bacteria, including two strains of *Mycobacterium smegmatis* (mc$^2$-6 and mc$^2$-155) and several non-MSH-producing species (*Escherichia coli* HB101, *Enterococcus faecalis* ATCC 29212, and *Streptococcus mutans* ATCC 33402) were grown as separate streaks on a single agar dish. A supported nitrocellulose membrane circle (NITROPURE®, 0.45 μm porosity, 81 mm diameter) was marked with a pencil for orientation on the plate, and pre-soaked in TBS. Excess TBS was drained from the membrane, a freshly-made solution of Pierce IMJECT® maleimide-activated BSA (265 μg in 13.3 ml TBS, to give 5 μg/cm$^2$ loading) added, and the membrane incubated for 30 min. Excess liquid was drained from the membrane, which was then laid onto the surface of the bacterial plate with care to avoid bubbles or smearing of the bacterial colonies. The membrane was lifted carefully and laid bacteria-side up for 1 h in a clean glass Petri dish containing a solution of N-acetylglucosaminidase (3.1 units in 10 ml,TBS adjusted to pH 4.2 with acetic acid). The membrane was next washed briefly with TBS to remove adhering cells and washed with 10 ml TBST. Excess liquid was drained and the membrane incubated in 10 ml 2% fish skin gelatin in TBS for 2 h. The membrane was drained, 10 ml affinity-purified anti-MSH IgG solution (containing ~18 μg total protein) added and incubated overnight at 4° C. on an orbital platform shaker set to 60 rpm. The antibody solution was aspirated and the membrane washed 3 times in TBST (10 ml and 10 min for each wash). Excess liquid was drained, 10 ml of secondary antibody (goat anti-rabbit [whole IgG] F(ab')$_2$ fragments conjugated to bovine intestinal alkaline phosphatase, diluted 1:15000 in TBS) added, and the membrane incubated for 1 h. The membrane was drained, washed twice in TBST and thrice in TBS (10 ml and 5 min each wash). Development was with BCIP-NBT (SigmaFAST®). After thoroughly washing in distilled water, the blot was air-dried. MSH-containing bacteria are revealed as dark purple stains; only the two strains of *M. Smegmatis* produced positive signals (FIG. 3).

Several methods were tested for lysing bacterial cells, including air-drying, heat (microwaving), treatment with enzymes (lysozyme and/or N-acetylglucosaminidase), and treatment with dilute organic solvent (20% v/v acetonitrile in water, applied as a fine spray over the cells on the membrane, five times in 20 minutes). All of these methods worked to some extent, but the dilute acetonitrile treatment and the N-acetylglucosaminidase treatment were found to give the best blots with the lowest background and are thus the preferred methods.

Example 7

Assay Specificity

Figure 4:
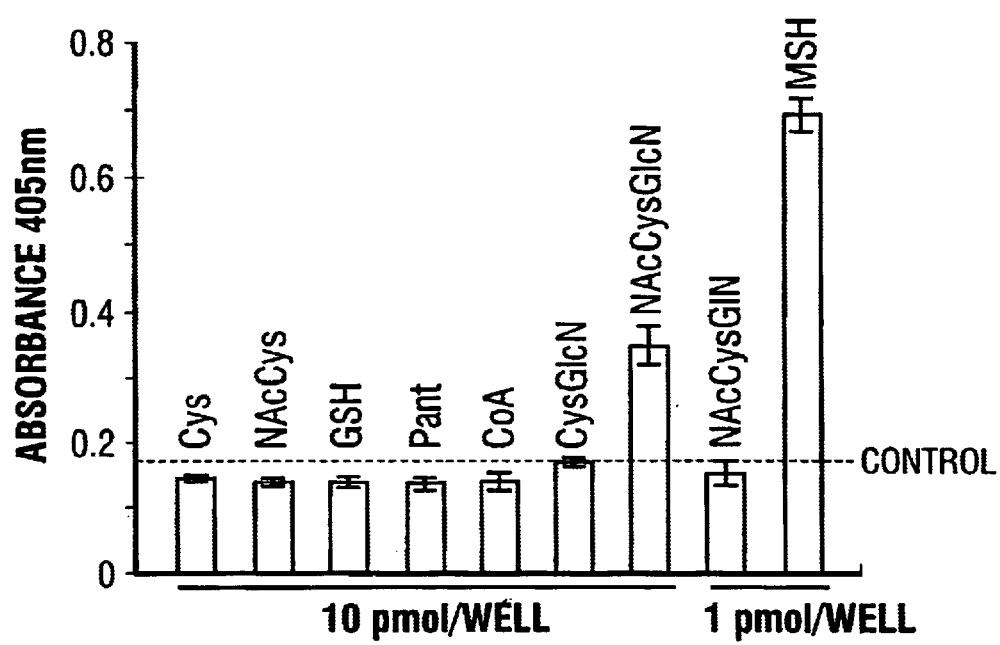
FIG. 4 illustrates results from an immunoassay using the ELISA procedure described in Example 4, using different low-molecular mass thiols to test for antibody specificity. Thiols were assayed at 1 or 10 pmol per well as indicated. Values are the mean of quadruplicate determinations with error bars indicating standard deviation from the mean. The control value is for wells that received maleimide-BSA with no thiol added.

Since reaction of typical cellular constituents with maleimide-BSA is largely limited to thiols, it was considered important to ascertain whether any typical biological thiols would produce false-positive assay results. The following thiols were tested in the ELISA protocol described above in Example 4: L-cysteine, glutathione, pantetheine, and coenzyme A. At the 10 pmol level all of these gave negative results indicating that these are not recognized by the anti-mycothiol antibody (FIG. 4).

In order to test whether the anti-mycothiol antibody recognizes component parts of the mycothiol molecule we also tested the ELISA on N-acetyl-L-cysteine, L-cysteinyl-glucosamine, (2-L-cysteinyl)amido-2-deoxy-α-D-glucopyranose), and N-acetyl-L-cysteinyl-glucosamine (2-N-acetyl-L-cysteinyl)amido-2-deoxy-α-D-glucopyranose). The first two gave negative results at the 10 pmol level but the latter compound, which has the structure of MSH with the inositol removed, gave a positive assay with a sensitivity of about 4% of that for MSH (FIG. 4).

Finally, in order to test whether the maleimide functionality was required for the immunoassay architecture as described in Example 4 to be successful, colony-lift blots were performed as described in Example 6. Blots with *M. smegmatis* run in parallel but with unmodified BSA in place of maleimide activated BSA produced no detectable signal, demonstrating that the maleimide functionality is indeed necessary for capturing released mycothiol, and that nonspecific binding of other inositol derivatives such as cell wall phosphatidylinositol mannosides does not result in false positives.

Example 8

Use of Mycothiol Linked to a Binding Agent in the Assay of Mycothiol

Immobilization of MSH for subsequent detection can also be achieved by taking advantage of the unique chemistry of the thiol functionality to link it to a binding agent. The binding agent, in this example biotin, is chosen based upon the availability of a substance, in this example a modified form of avidin, having a high affinity for the binding agent. The binding agent is linked to a thiol-reactive group, in this example maleimide, which reacts with the thiol moiety of mycothiol.

The following assay architecture illustrates an example of this method.

1. MSH is biotinylated with a thiol-specific reagent. Biotin is an example of a small molecule that can be bound specifically by a protein (in this case, avidin); biotin-avidin systems offer the advantage of extremely strong non-covalent binding.
2. The biotinylated mycothiol is captured by avidin which has previously been attached to the microtiter plate. Unmodified avidin can be replaced by modified (e. g., deglycosylated) avidin products that exhibit lower non-specific binding than unmodified avidin.
3. The inclusion of an organic solvent, i. e., acetonitrile, in the aqueous buffer that is used to dissolve the antigen increases the efficiency of capture by the immobilized avidin of the biotinylated mycothiol.
4. Anti-MSH antibody is allowed to bind to the immobilized biotinylated mycothiol.
5. Alkaline phosphatase-labelled goat-anti-rabbit IgG (F(ab')$_2$ fragments), is allowed to bind to the anti-MSH antibody, and pNPP is used to quantitate the amount of bound alkaline phosphatase. Other reporter enzyme-secondary antibody conjugates may be used.

This immunoassay is depicted in the schematic below:

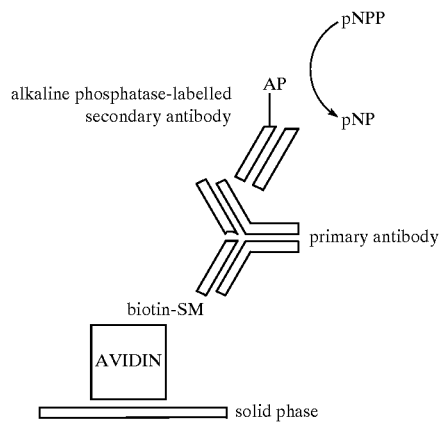

An example of a specific experimental procedure for this type of immunoassay follows.

Preparation of MSH-MPB Standards

To produce biotinylated MSH suitable for use as a standard, the following procedure was carried out: 5.0 μL of 3.7 mM pure MSH in 0.1% TFA was added to 12.3 μL 1.5 mM MPB in DMSO/acetonitrile/100 mM phosphate buffer, pH 7.0 (1:4:5). The mixture was allowed to react 1 hour at room temperature. To determine the extent of biotinylation, unreacted MSH was measured by titration with DTNB. The standard was stored in 1.0 μL aliquots frozen at −70° C. For use in ELISA analyses, the standard was diluted to a concentration of 1.0 μM in Tris-buffered saline, pH 7.3, containing 0.04% w/v sodium azide, 0.05% v/v Tween 20 and 0.1% w/v BSA (TBSTB); this solution was stable for several (>6) months when stored refrigerated as indicated by consistency of ELISA measurements.

ELISA Procedure

1. NeutrAvidin (Pierce) was diluted in TBS to a final concentration of 6 ng/μL and 100 μL aliquots (equivalent to 600 ng NeutrAvidin) added to each well of a microtiter plate (Immulon 4).
2. The sealed plate was incubated overnight at 4° C.
3. The wells were drained and washed once with TBST. The antigen (biotinylated MSH, see above) was diluted appropriately in TBST containing 0.5% w/v BSA ("TBSTB") and varying percentages by volume of CH$_3$CN, and added in 100 μL aliquots to the wells. The plate was sealed and incubated overnight at 4° C.
4. The wells were drained and blocked with 1% FSG/TBS, 1 hour at room temperature.
5. The wells were washed once with TBST. 100 μL of affinity-purified anti-MSH, diluted to a final concentration of 0.5 ng/μL in TBSTB, was added to each well. The plate was incubated 2 hours at 37° C.
6. The wells were washed twice with TBST. 100 μL of goat anti-rabbit IgG, alkaline phosphatase-labelled F(ab')$_2$ fragments (Sigma), diluted 1:1500 in TBSTB, was added to each well. The plate was incubated 1 hour at room temperature.
7. The wells were washed four times in TBST. The plate was then developed with 200 μL per well of freshly-made pNPP (1 mg/mL in 1 M diethanolamine, pH 9.8, containing 0.4 mM MgCl$_2$). Development was stopped with the addition of 50 μL per well of 4 M NaOH. Absorbance was measured at 405 nm.

Figure 5:
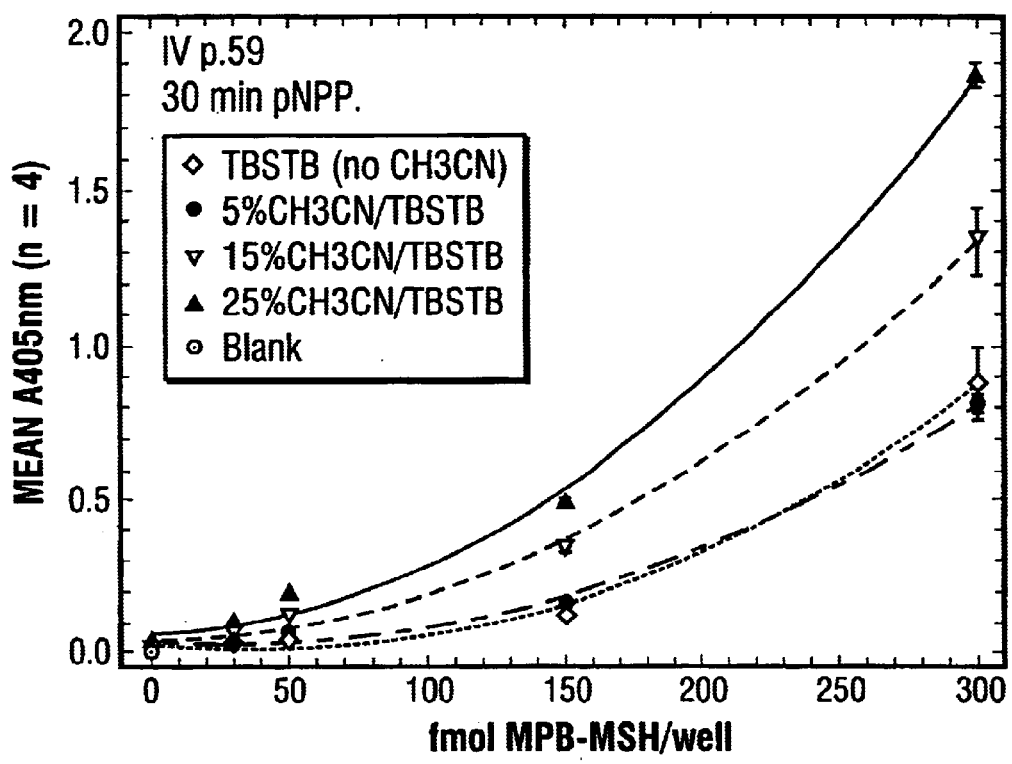
FIG. 5 shows results from an immunoassay using the ELISA procedure described in Example 8, that demonstrated the effect of increasing the percentage by volume of acetonitrile in the buffer used for the antigen-binding step ("binding buffer"). Increasing the binding buffer's acetonitrile content from 0% to 25% by volume results in an approximate doubling of the observed signal.
Figure 6:
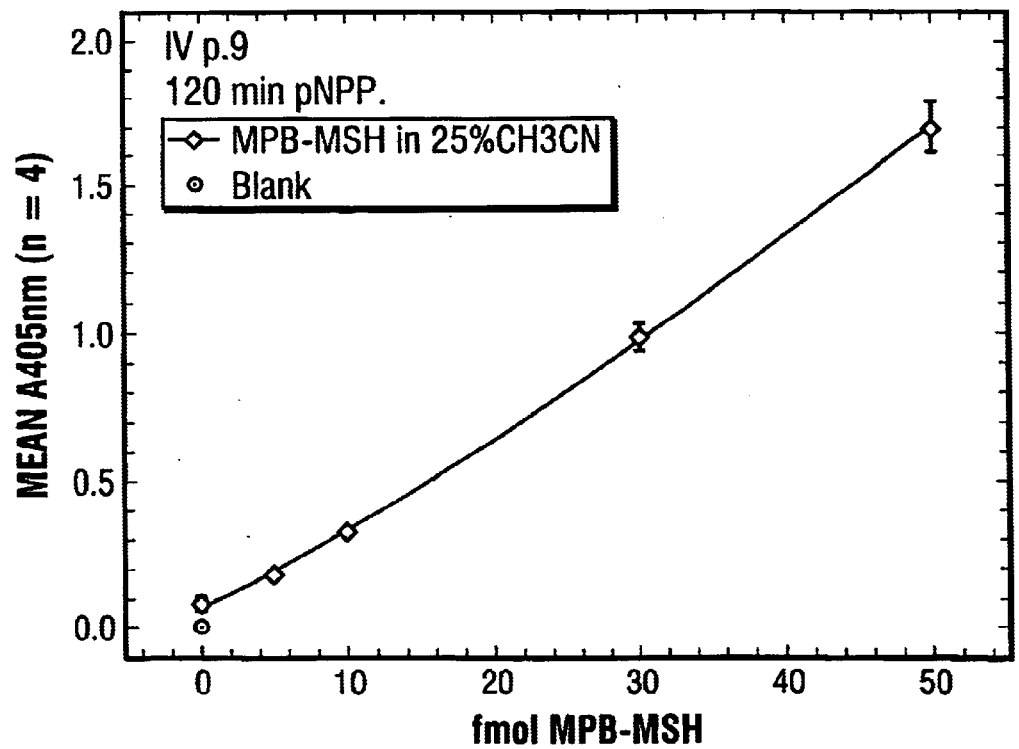
FIG. 6 shows results from an immunoassay using the ELISA procedure described in Example 8, demonstrating the increase in signal and negligible increase in background resulting from an extended (120 minute) development period. Biotinylated mycothiol (MPB-MSH) was applied in 25% v/v acetonitrile in TBS.

The results of two experiments are illustrated in FIGS. 5 and 6. FIG. 5 shows results from an experiment that demonstrated the effect of increasing the percentage by volume of organic solvent (i. e., acetonitrile) in the buffer ("binding buffer") used for the antigen-binding step. Increasing the binding buffer's acetonitrile content from 0% to 25% by volume results in an approximate doubling of the observed signal. Further experiments (data not shown) demonstrate that increasing the binding buffer's acetonitrile content from 25% to 50% by volume results in an additional increase in signal of approximately 170%. No increase in background noise is observed by the addition of acetonitrile to the binding buffer. Therefore, the inclusion of acetonitrile in the binding buffer is an important method for increasing the overall sensitivity of this assay.

FIG. 6 shows results from an experiment that demonstrated the increase in signal and negligible increase in background resulting from an extended (120 minute) development period. Our initial experiments show this immunoassay method to be highly sensitive with a useful range (dependent primarily on development time) of about 5–300 fmol MSH, and a detection limit of at least 5 fmol MSH, that is to say, about 3 orders of magnitude more sensitive than our HPLC assay.

Example 9

Detection of Mycothiol by a Dot Blot Immunoassay

The immunoassay described in Example 8 was adapted for use in a dot blot assay. An example of a specific experimental procedure for this type of immunoassay follows.

1. A piece of polyvinylidene fluoride (PVDF) membrane (Millipore Immobilon P, 0.45 µm porosity) was pre-wet by immersion in methanol (10 min) followed by immersion in Tris-buffered saline, pH 7.3, containing 0.04% w/v sodium azide ("TBS", 20 min).
2. The pre-wet membrane was assembled in the dot blot apparatu's(BioRad BioDot) according to the manufacturer's instructions, and the membrane re-wetted by passing 50 µL/well TBS by vacuum.
3. NeutrAvidin (Pierce) was diluted in TBS to a final concentration of 0.4 µg/µL. A 50 µL aliquot (equivalent to 20 µg NeutrAvidin) followed by a wash of 20 µL TBS was added to each well and allowed to pass through the membrane by gravity.
4. The membrane was blocked with 100 µL per well of a 2% (v/v) fish-skin gelatin solution in TBS, allowed to pass through by gravity.
5. The membrane was washed with two 400 µL volumes per well of TBS containing 0.05% v/v Tween 20 ("TBST"), passed through by vacuum.
6. The antigens (biotinylated mycothiol, see Example 8) were prepared in 50% (v/v) acetonitrile in phosphate-buffered saline, pH 7.2, quadruplicate samples from 0 to 0.3 pmol applied per well in 500 µL volumes, and allowed to pass through by gravity. Blank wells received only the buffers and blocking agent.
7. The membrane was washed with two 400 µL volumes per well of TBS containing 0.05% v/v Tween 20 ("TBST"), passed through by vacuum.
8. Affinity-purified anti-MSH was diluted to a final concentration of 1 ng/µL in TBST containing 0.1% w/v BSA ("TBSTB"), and 50 µL added to each well and allowed to pass through by gravity.
9. The membrane was washed with two 400 µL volumes per well of TBS containing 0.05% v/v Tween 20 ("TBST"), passed through by vacuum.
10. Fifty µL of goat anti-rabbit IgG, alkaline phosphatase-labelled F(ab')$_2$ fragments (Sigma), diluted 1:3000 in TBSTB, was added to each well and allowed to pass through by gravity.
11. The membrane was washed with two 400 µL volumes per well of TBS containing 0.05% v/v Tween 20 ("TBST"), passed through by vacuum. The membrane was removed from the dot blot apparatus amd washed in three 50 µL volumes of TBS. Excess TBS was drained, and to the wet membrane was added 10 µL of a freshly-made solution of 5-bromo4-chloro-3-indolyl phosphate/nitroblue tetrazolium ("SigmaFAST" BCIP/NBT alkaline phosphatase substrate). The purple color was allowed to develop for 3 minutes, after which excess substrate was washed from the membrane by rinsing in deionized water.

Figure 7:
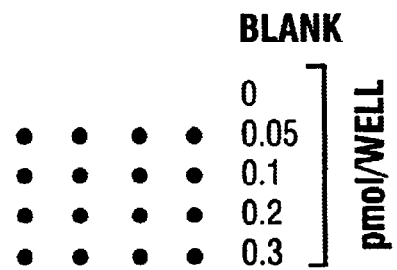
FIG. 7 illustrates the dot blot described in Example 9. Biotinylated mycothiol samples were assayed from 0 to 0.3 pmol per well in quadruplicate.

Results from this type of assay (FIG. 7) demonstrated that the assay had a detection limit of about 0.05 pmol (50 fmol) per well. Though it does not have the working range of an ELISA type assay (as described in Example 8), it is useful for qualitative detection of mycothiol, for example in the assay of bacterial cell lysates for the presence of mycothiol.

Example 10

Use of Mycothiol Modified with a Detectable Label and of Anti-mycothiol Antibody Prebound Via an Antibody-binding Agent to a Solid Phase in the Assay of Mycothiol Immobilization of mycothiol for subsequent detection can be achieved by first modifying mycothiol with a detectable label, capturing the modified MSH via an anti-MSH antibody prebound to a solid phase, and finally detecting the label. One specific method (binding of biotinylated MSH to anti-MSH antibody prebound via protein A to a solid phase) illustating this assay architecture is outlined below.

1. Protein A is bound to a high-binding microtiter plate by non-specific adsorption.
2. Affinity-purified rabbit anti-MSH IgG is then allowed to bind to the protein A-coated wells.
3. MSH is biotinylated with the thiol-specific reagent 3-(N-maleimidopropionyl)biocytin ("MPB").
4. The biotinylated MSH is captured by the anti-MSH antibody and thus immobilized on the plate.
5. Alkaline phosphatase-labeled avidin is allowed to bind to the immobilized biotinylated mycothiol, and pNPP is used to quantitate the amount of bound alkaline phosphatase. (Other avidin derivatives could be used to quantitate the amount of captured MSH-biotin.)

This immunoassay is depicted in the schematic below:

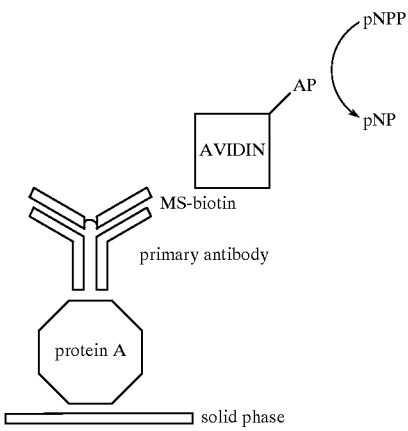

An example of a specific experimental procedure for this type of immunoassay follows.

Preparation of MSH-MPB Standards

Biotinylation of MSH standards is carried out as described in Example 8.

ELISA Procedure

Generally for each 96-well plate, eight wells received only the blocking solution and all washes. Four of these were used as a blank; the remaining four were used for measuring known amounts of the reporter enzyme (alkaline phosphatase-labelled avidin). One hundred $\mu$L of a 6 ng/$\mu$L protein A solution in Tris-buffered saline, pH 7.3, containing 0.04% w/v sodium azide (TBS) was added to each well of a microtiter plate (Immulon-4, 96-well flat-bottomed microtiter plates Dynatech) which was then sealed with tape and incubated 5 h at 37° C. The wells were thoroughly drained by aspiration with gentle vacuum, and blocked with 400 $\mu$L of a 1% (v/v) solution of fish-skin gelatin (Sigma) in TBS, 1 h @ r. t. The wells were drained, 100 $\mu$L of primary antibody (2 ng/$\mu$L affinity-purified rabbit anti-MSH IgG in TBSTB) added per well, the plate re-sealed and incubated at least overnight (>14 h) at 4° C. The wells were drained and washed once with 400 $\mu$L/well TBS containing 0.04% w/v sodium azide and 0.05% v/v Tween 20 (TBST). The antigens (standards or unknowns), diluted to contain an identical percentage of $CH_3CN$, were added to the wells, the plate sealed, and incubated 3.5 h at 37° C. Wells were drained, washed once with 400 $\mu$L/well TBST, 100 $\mu$L/well of alkaline phosphatase-labelled avidin (Sigma ExtrAvidin-Alkaline Phosphatase) at a concentration of 0.5 ng/$\mu$L in TBSTB added, and the plate sealed and incubated 1 h at r. t. Wells were drained, washed once with 400 $\mu$L/well TBST, then three times with 200 $\mu$L/well TBST. The first three wash volumes were removed by sharply tapping the plate upside down, and the last wash volume removed by aspiration. Two $\mu$L (1 ng) of the alkaline phosphatase-labelled avidin solution were added to two of the wells that received only the blocking solution and wash buffers. The plate was then developed with 200 $\mu$L per well of freshly-made pNPP (1 mg/mL in 1 M diethanolamine, pH 9.8, containing 0.4 mM $MgCl_2$). Absorbance was measured at 405 nm. For time-point readings, the plate was read at successive time points without the addition of any stop solution. For a single end-point reading, pNPP development was stopped with the addition of 50 $\mu$L per well of 4 M NaOH.

Figure 8:
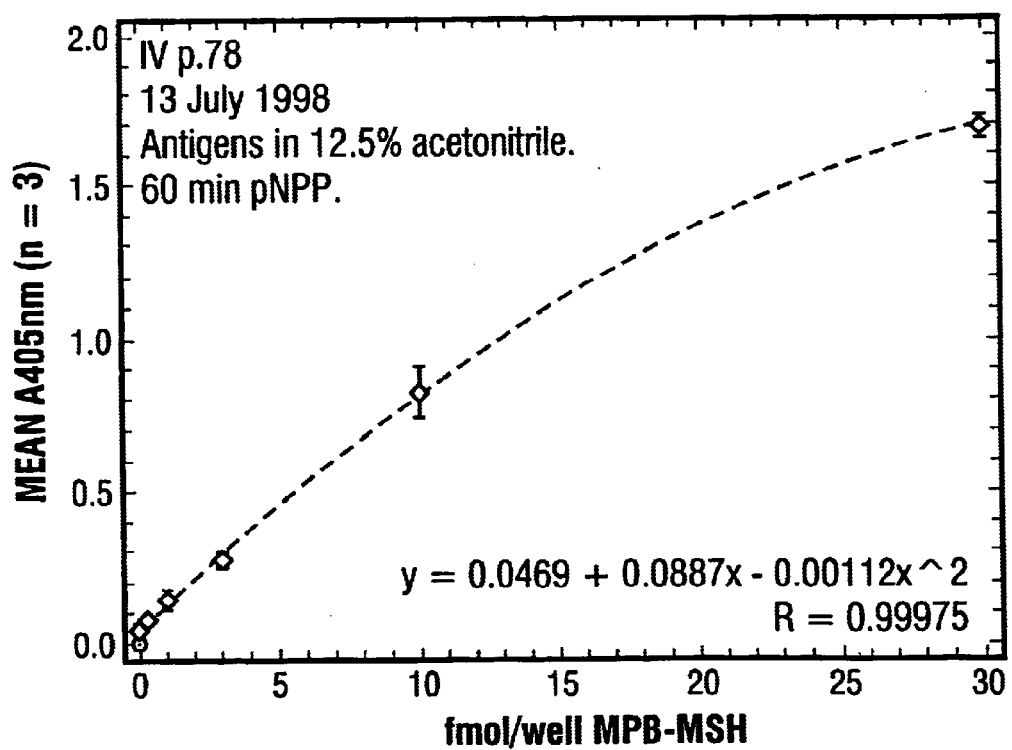
FIG. 8 is a typical standard curve obtained using the ELISA procedure described in Example 10, using biotinylated mycothiol from 0.3–30 fmol per well. Samples were run in triplicate; error bars indicate standard deviation from the mean. Closed diamonds=biotinylated mycothiol samples; open circle=blank.

FIG. 8 shows results from an immunoassay utilizing the above procedure. Wells received 600 ng protein A, 200 ng anti-MSH antibody, and 50 ng alkaline phosphatase-labelled avidin. Antigens were applied in 12.5% $CH_3CN$ in TBS. The data shown are from 60 min development with pNPP and no stop solution.

Our initial experiments using this immunoassay architecture as described above showed that it has a broad working range (primarily dependent on development time) of at least 0.3–300 fmol MSH and a detection limit of at least 0.3 fmol MSH, that is to say, this architecture is of even higher sensitivity than the immunoassay methods described in examples 4, 12, and 13, and approximately 4 orders of magnitude more sensitive than our HPLC assay (Newton et al., 1993. *J. Bacteriol.*, 175:2734; Newton et al., 1996, *J. Bacteriol.*, 178:1990).

Example 11

Detection of Mycothiol from Mycobacterial Cells in Human Biological Fluids

A further variation utilizing the immunoassay architecture described in Example 10 involves carrying out the biotinylation reaction in a non-homogeneous mixture consisting of the aqueous cell suspension and a solution of the biotinylating reagent in an organic solvent that is immiscible with water. An important advantage of this method is that, because the organic solvent used for dissolving the biotinylation reagent is not miscible with water, subsequent to biotinylation, the aqueous phase (now containing the biotinylated mycothiol) can be removed from the organic phase and analyzed with no need for dilution. The method of capture and detection of antigen is identical to that previously described.

Two examples of a specific experimental procedure for this type of immunoassay follow. The first example demonstrates detection of mycothiol from mycobacterial cells in human urine. The second example demonstrates detection of mycothiol from mycobacterial cells in human cerebrospinal fluid. This second example also demonstrates the effectiveness of adding nutrients such as glucose and glycerol to the sample in order to increase the mycothiol content of the bacterial cells.

Preparation of MSH-MPB Standards

Biotinylation of MSH standards is carried out as described in Example 8.

Biotinylation of MSH from *Mycobacterium avium* Cells in Urine

*Mycobacterium avium* was grown in Middlebrook 7H9 medium supplemented with 0.4% w/v glucose and 0.05% v/v Tween-80. Cells used in experiments were harvested at early- to mid-log phase growth, and diluted in fresh medium appropriately to give concentrations ranging from ~3×10$^3$ cfu to 3×10$^4$ cfu in a volume of 10 $\mu$L. To each microfuge tube was added 10 $\mu$L cell suspension and 990 $\mu$L sterile-filtered urine. The tubes were capped, vortexed, centrifuged 10 minutes at 13,000 rpm, and 990 $\mu$L of supernatant carefully removed without disturbing the pelleted cells. To the residual 10 $\mu$L in each tube was added in order: 100 $\mu$L 10 mM phosphate buffer, pH 7.2, 3 $\mu$L 80 mM EGTA, pH 8.6, 2.4 $\mu$L 600 mM phosphate buffer, pH 10.7. The final pH of this mixture was 8.0. A 10 mM solution of 3-(N-maleimidopropionyl)biocytin (MPB) in DMSO was prepared shortly before use. This was diluted immediately before reaction to 6 $\mu$M in water-saturated $CHCl_3$ at room temperature, and 120 $\mu$L of this solution added to each sample tube. The tubes were capped, vortexed, and immediately incubated in a water bath 10 min at 37° C. with further vortexing at 5 minute intervals. Five $\mu$L of a freshly-made solution of 175 $\mu$M 2-mercaptoethanol was added to each tube to react with excess MPB, the tubes capped, shaken, and incubated a further 5 min at 37° C. The samples were stored overnight at 40° C. before analysis by ELISA. For analysis, the tubes were centrifuged 1 minute at 13,000 rpm, and 100 $\mu$L of the top aqueous phase in each tube carefully removed for analysis.

ELISA Procedure

The ELISA procedure is identical to that described in Example 10 above, except that as the samples are essentially aqueous and could be applied to the microtiter wells without further dilution, the standards are prepared in 20 mM phosphate buffer, pH 8.0

Figure 9:
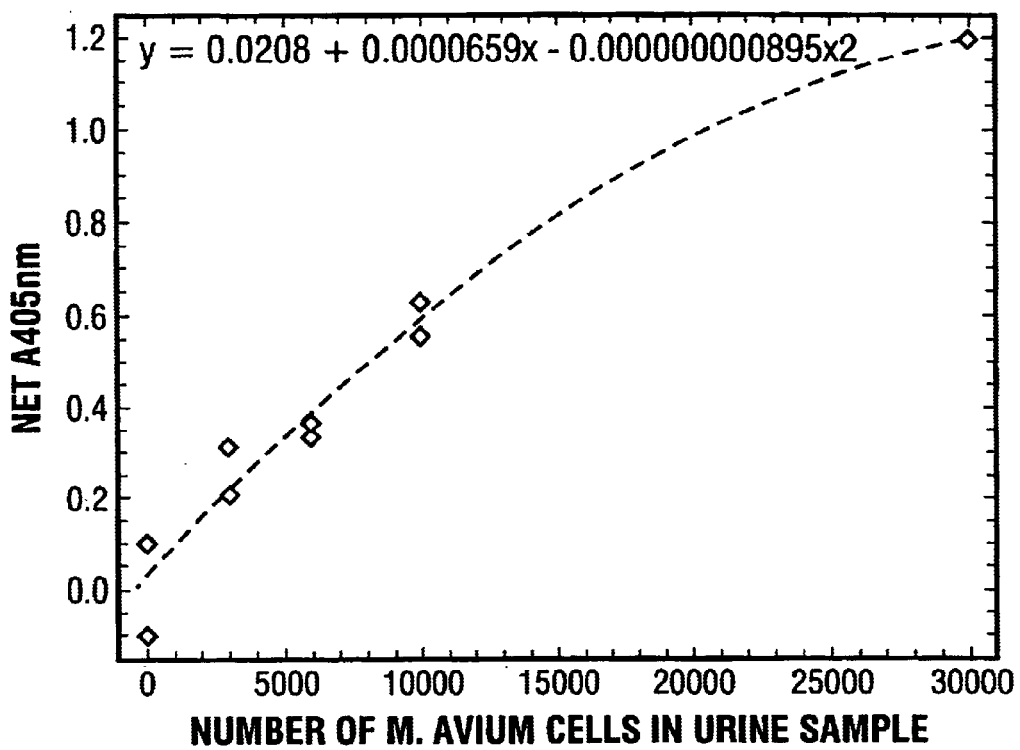
FIG. 9 shows results from the immunoassay described in Example 11, assaying *Mycobacterium avium* cells in human urine.

FIG. 9 shows results from an immunoassay utilizing the above procedure. Wells received 600 ng protein A, 200 ng anti-MSH antibody, and 50 ng alkaline phosphatase-labelled avidin. Samples were 1.00 mL volumes of *Mycobacterium avium* cells in urine, biotinylated as described above, and 100 $\mu$L of the aqueous phase analyzed. The data shown are from 40 min development with pNPP and no stop solution.

Mycothiol recovered from *Mycobacterium avium* cells seeded into urine using this protocol was 68% of that found by direct analysis of samples from the same stock of cells in phosphate buffer without centrifugation. Independent analysis by plating indicated a similar recovery from centrifugation and resuspension of the cells so most of the ~35% loss can be attributed to the centrifugation step.

Biotinylation of MSH from *Mycobacterium avium* Cells in Cerebrospinal Fluid

*Mycobacterium avium* was grown in:Middlebrook 7H9 medium supplemented with 0.4% w/v glucose and 0.05% v/v Tween-80. Cells used in experiments were harvested at early- to mid-log phase growth, and diluted in fresh medium appropriately to give concentrations ranging from ~3×10$^3$ cfu to 3×10$^4$ cfu in a volume of 10 $\mu$L. Sterile-filtered cerebrospinal fluid ("CSF") was divided into two portions, one of which (referred to as "enriched CSF") received the addition of 1% (v/v) glycerol and 0.5% (w/v) glucose. To each microfuge tube was added 10 $\mu$L cell suspension and 990 $\mu$L of either CSF or enriched CSF. The tubes were capped, vortexed, centrifuged 10 minutes at 13,000 rpm, and 990 $\mu$L of supernatant carefully removed without disturbing the pelleted cells. To the residual 10 $\mu$L in each tube was added 100 $\mu$L 10 mM phosphate buffer, pH 7.2, followed by 5.4 $\mu$L 44.4 mM EGTA in 267 mM phosphate buffer, pH 9.0. The final pH of this mixture was 8.0. A 10 mM solution of 3-(N-maleimidopropionyl)biocytin (MPB) in DMSO was prepared shortly before use. This was diluted immediately before reaction to 6 $\mu$M in water-saturated CHCl$_3$ at room temperature, and 120 $\mu$L of this solution added to each sample tube. The tubes were capped, vortexed, and immediately incubated in a water bath 10 min at 37° C. with further vortexing at 5 minute intervals. Five $\mu$L of a freshly-made solution of 175 $\mu$M 2-mercaptoethanol was added to each tube to react with excess MPB, the tubes capped, shaken, and incubated a further 5 min at 37° C. The samples were stored overnight at 40° C. before analysis by ELISA. For analysis, the tubes were centrifuged 1 minute at 13,000 rpm, and 100 $\mu$L of the top aqueous phase in each tube carefully removed for analysis.

ELISA Procedure

The ELISA procedure is identical to that described immediately above for samples from human urine.

Figure 10:
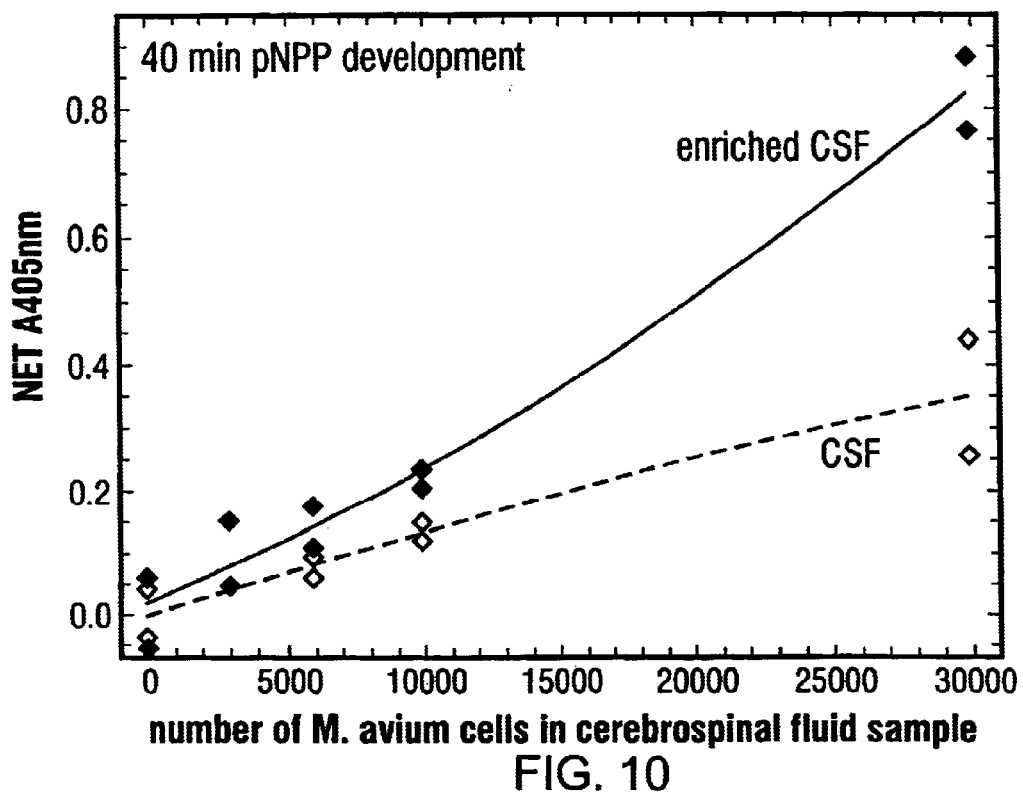
FIG. 10 shows results from the immunoassay described in Example 11, assaying *Mycobacterium avium* cells in either cerebrospinal fluid with no additives ("CSF") or cerebrospinal fluid with glucose and glycerol added ("enriched CSF"). Note that the addition of glycerol and glucose to the mycobacterial cell suspension roughly doubles the amount of mycothiol detected.

FIG. 10 shows results from an immunoassay utilizing the above procedure. Wells received 600 ng protein A, 200 ng anti-MSH antibody, and 50 ng alkaline phosphatase-labelled avidin. Samples were 1.00 mL volumes of *Mycobacterium avium* cells in either cerebrospinal fluid or enriched cerebrospinal fluid, biotinylated as described above, and 100 $\mu$L of the aqueous phase analyzed. The data shown are from 40 min development with pNPP and no stop solution. Note that the addition of glycerol and glucose to the mycobacterial cell suspension roughly doubles the amount of mycothiol detected.

Example 12

Detection of Mycothiol-producing Bacteria on Microtiter Plates

The immunoassay methods described above can be adapted easily for use in screening large numbers of bacteria, for example a library of strains grown in a microtiter plate. The specific example given here makes use of the immunoassay architecture described in Example 10.

Biotinylation of MSH from Cells Grown in a Microtiter Plate

To demonstrate the utility of the immunoassay for screening individual bacterial strains for mycothiol production, three different strains of *Mycobacterium smegmatis* mc$^2$155 that together spanned the range of MSH production were used. Included as a positive (i. e., containing normal high levels of MSH) control was the parent strain of mc$^2$155, and as a negative control, strain 49 (Newton et al., submitted) which produces no detectable MSH. A third control, strain 164 (our unpublished data), was included as an example of an MSH-deficient strain that produces a reduced but detectable level of MSH. The strains were grown to early logarithmic phase in Middlebrook 7H9 medium supplemented with 0.4% w/v glucose and 0.05% v/v Tween-80. Each strain was diluted in medium to an initial concentration of 10$^8$ cfu/mL, then further diluted in series as required. To each well of an Immulon-4 96-well microtiter plate was added a 100 $\mu$L aliquot of these serially diluted cell suspensions, so that the number of cells per well encompassed the range 0 to 10$^7$ cells (in duplicate) for each of the three strains. A 10 mM solution of 3-(N-maleimidopropionyl)biocytin (MPB) in DMSO was prepared shortly before use. This was diluted immediately before reaction to 6 $\mu$M in room temperature CH$_3$CN. Additions of the reagents to the microtiter plate was made by means of a multichannel pipetter. To each well was added 20 $\mu$L 0.1 M Na$_2$HPO$_4$ (pH unadjusted), followed by 120 $\mu$L 6 $\mu$M MPB in CH$_3$CN. The plate was covered and incubated in a water bath at 60° C. for 15 minutes. To block unreacted MPB, to each well was added 20 $\mu$L 60 $\mu$M 2-mercaptoethanol in water (giving a final biotinylation reaction volume of 260 $\mu$L per well), and the plate covered and incubated a further 5 minutes at 60° C. The plate was then stored overnight at 4° C. prior to analysis.

ELISA Procedure

The ELISA procedure was carried out as described in Example 10. The ELISA plate wells were coated with protein A, gelatin, and anti-MSH antibody, and washed once with TBST as described. The drained ELISA wells each then received 75 $\mu$L TBS and 25 $\mu$L of the biotinylated cell extracts; each thus contained 25/260 or 9.6% of the original biotinylated cell extract volume, in a final CH$_3$CN concentration of 12.5%. Standards were also applied in 12.5% acetonitrile in TBS. The rest of the analysis was performed as described in Example 10.

Figure 11:
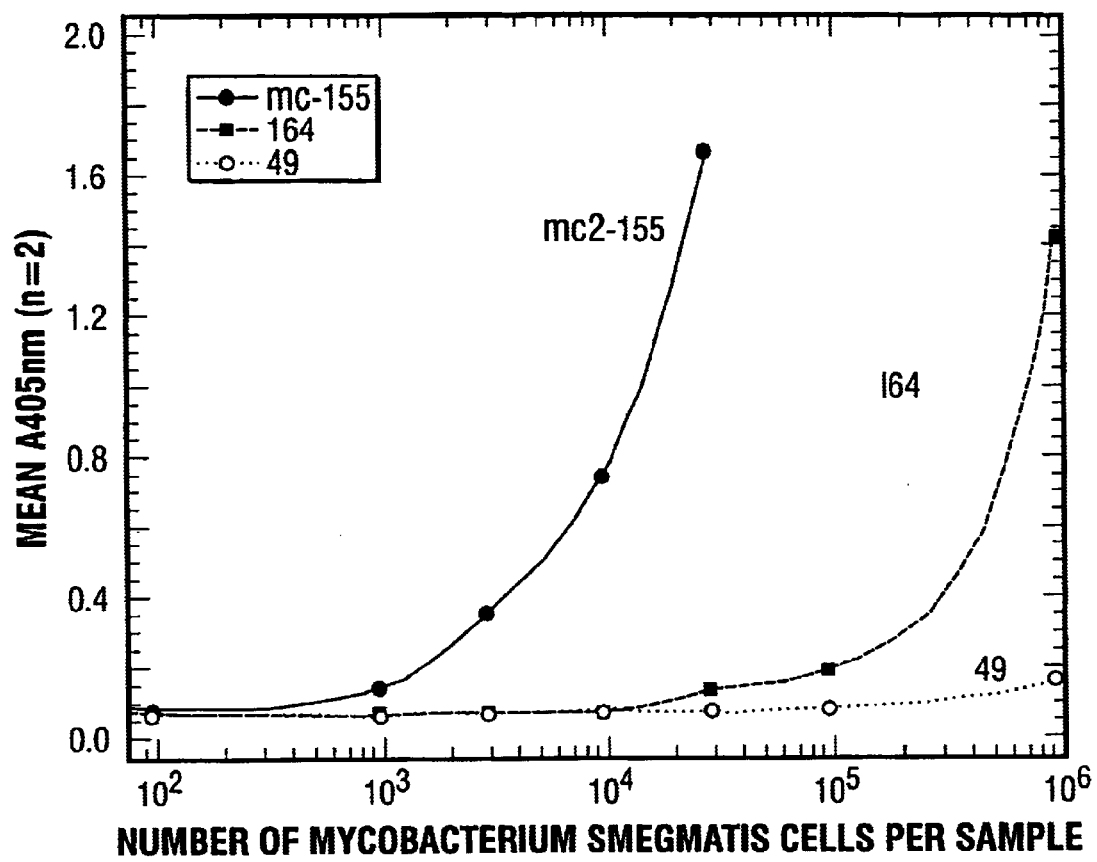
FIG. 11 shows results from the immunoassay described in Example 12. Data shown are means of 2 samples. *Mycobacterium smegmatis* mc$^2$155 (solid circles) is a parent strain known to produce high levels of mycothiol, strain 49 (open circles) is a mutant strain known to produce no mycothiol, and strain 164 (solid squares) is a mutant strain which produces reduced levels of mycothiol.

FIG. 11 shows results from an immunoassay utilizing the above procedure. Wells received 600 ng protein A, 200 ng anti-MSH antibody, and 50 ng alkaline phosphatase-labelled avidin. Both standards and biotinylated cell extracts were applied in a final CH$_3$CN concentration of 12.5%. The data shown are from 60 min development with pNPP and no stop solution.

Independent determinations of the mycothiol content of strains mc$^2$155, I64, and 49 were carried out numerous times using HPLC analysis of the monobromobimane-treated cell extracts (Table 2) (Anderberg et al., *J. Biol. Chem.*, 1998 in press; Newton et al., submitted; our unpublished data for I64). The MSH content of strain I64 is low but measurable, and is about 2 orders of magnitude less than that of the parent strain mc$^2$155 (our unpublished data). This compares well with the results obtained by immunoassay as shown in FIG. 11. The MSH content of strain 49 is below detectable levels (Newton et al., submitted) using our published HPLC methods (Newton et al., 1993, *J. Bacteriol.*, 175:2734; Newton et al., 1996, *J. Bacteriol.*, 178:1990), and by immunoassay with 60 minutes development time is barely above background only at the highest number (~10$^6$) of cells assayed. In the case of the parent strain mc$^2$155 which contains the highest levels of MSH, the lowest number of cells detectable in this particular experiment was approximately 3000 cells.

TABLE 2

| Mycobacterium smegmatis mc²155 strain | MSH content by HPLC analysis (μmoles per gram residual dry weight) |
|---|---|
| mc²155 (parent strain) | 10 |
| 164 | 0.05 |
| 49 | <0.004 |

Example 13

Mycothiol Releasing Materials and Methods

The first step in preparing a bacterial sample for analysis of mycothiol is to obtain a cell pellet and to wash it to remove the bulk of the original suspending medium. For most fluid samples this can be achieved by centrifugation. For some samples, notably sputum, this is a much more difficult task. Centrifugation of a 1 ml sputum sample reduces the volume by a factor of only 3–4, leaving the bacterial cells contaminated with a large amount of sputum fluid. Some form of treatment is required to produce a sufficiently compact pellet for analysis. In this example, standard and modified treatments for liquefaction of sputum are identified. This example illustrates an incubation protocol useful in preparing samples for analysis because it increases the mycothiol content of mycobacteria, and an example of a typical cell pellet analysis protocol applied to measure mycothiol in *M. avium*, a species that infects AIDS patients, is given.

Sputum samples (1 ml each from a mixture of sputum pooled from several patients and homogenized) seeded with *M. avium* at $10^6$ cell per ml were diluted with an equal volume of one of the following liquefying agents, mixed thoroughly by vortexing, and then incubated as indicated.

1. 1% w/v, 3% w/v sodium dodecyl sulfate; 40 min @ 22° C.;
2. 2% w/v NaOH; 15 min @ 22° C.;
3. 25% w/v trisodium phosphate: 40 min @ 22° C.;
4. 1% w/v cetylpyridinium chloride, 2% w/v NaCl; 40 min @ 22° C.;
5. 10 mg/mL proteinase K, 2% w/v SDS; 40 min @ 37° C.'
6. 1 unit/ml neuraminidase; 40 min @ 37° C.

The samples were then diluted with PBS to a volume of 12 ml, vortexed well, and centrifuged 15 min at 1500×g. The supernatant was aspirated off, leaving the cell pellet undisturbed. This wash step was repeated once more. The final cell pellet was resuspended in 1 ml PBS, transferred to a microfuge tube, and centrifuged 15 min at 13000×g to a final cell pellet whose volume was recorded prior to lysis. The volumes of the final cell pellets were as follows:

| Treatment | Average volume of cell pellet (μL) |
|---|---|
| PBS(control) | 300 |
| 1% w/v NaOH, 3% w/v SDS | 10 |
| 2% w/v NaOH | 10 |
| 25% w/v trisodium phosphate | 10 |
| 1% w/v cetylpyridinium chloride, 2% w/v NaCl | 30 |
| 10 mg/ml proteinase K, 2% w/v SDS | 10 |
| 1 unit/ml neuraminidase | 150 |

All treatments gave acceptable reduction of pellet volumes over that of the control except the treatment with neuraminidase.

These treatments expose the cells to extended periods without nutrients, conditions that might result in depletion of the cellular mycothiol content. Incubation in enriched medium as a means of enhancing mycothiol content was tested with *M. smegmatis*. Resuspension of *M. smegmatis* cell pellets ($10^5$–$10^6$ cells) in 1 ml PBS containing 1% glycerol, 0.5% glucose, and Middlebrook 7H9 salts and incubation at 37° C. for 20 min prior to repelleting and analysis increased the mycothiol content by a factor of two. Increasing the incubation time to 1 hour gave no further increase in mycothiol content. Modification of the final wash step in the above sputum treatment protocols to use the 20 min incubation in nutrient rich medium is recommended.

*M. avium* is one of the more difficult mycobacteria to detect by mycothiol analysis because its mycothiol content is only about 30% that of *M. tuberculosis* and −20% that of *M. smegmatis* (Newton et al., 1996, supra), but it could be adequately measured by the current methods. Warm acetonitrile (50 μl 60° C.) was added to cell pellets ($10^5$–$10^6$ cells) of *M. avium* and the mixture incubated 15 min at 60° C. After centrifuging 5 min in a microcentrifuge at 12,000 rpm, 48 μl of supernatant was removed and mixed with 72 μl maleimide activated BSA (Pierce, 5 ng per μl in TBS with 0.04% $NaN_3$). The mixture was incubated 2 hours at room temperature and assayed by ELISA. The mean and standard deviation from 3 independent experiments was 1.4±0.4 pmol MSH per $10^6$ cells. This value is about half the value measured by HPLC on much larger samples of *M. avium* grown under different conditions (Newton et al., 1996, supra).

Example 14

Analysis of GleN and GlcN-Ins

Several standard methods of fluorescent amine labeling in conjunction with HPLC were tested initially with GlcN as potential ways to determine GlcN and GlcN-Ins. Reaction with dansyl chloride, fluorescamine, 12-(N-methyl-N-(7-nitrobenz-2-oxa-1,3-diazol-4-yl)) and CBQCA (Molecular Probes) provided markedly poorer sensitivity than labeling with AccQ-Fluor, a reagent recently developed for analysis of amino acids (Cohen, et. al 1993 supra). For labeling of aminosugars, a buffer of slightly lower pH than employed with amino acids was chosen so that the aminosugars, whose ammonium forms have lower pKa values than those of most amino acids, would have a competetive advantage during labeling of cell extracts. Detailed experimental methods follow.

Reagents—AccQ-Fluor was purchased from Waters. ATP, AcCys, GlcN-HCl, HEPES, inositol, NEM, sucrose, Tris, and yeast extract were obtained from Sigma. Cys and DTT were from Calbiochem, $^4$C-inositol was from NEN Life Science Products, glucose and Tween 80 were from Fisher, and acetonitrile was from Mallinckrodt. Atto-Tag CBQCA, dansyl-chloride, flourescamine, mBBr, and 12-(N-methyl-N-(7-nitrobenz-2-oxa-1,3-diazol-4-yl)) chloride were purchased from Molecular Probes. Methanesulfonic acid was supplied by Fluka. All other reagents were reagent grade or higher quality.

Preparation of 1-D-myo-Inosityl-2-amino-2-deoxy-α-D-glucopyranoside (GkcN-Ins)—GlcN-Ins was purified from *M. echinospora* (NRRL B-12180) by a modification of the method of Maehr et al. (Maehr, H., et al., 1980, *J. Antibiot.* (Tokyo) 33:1431–1435). *M. echinospora* was cultured on 0.5% yeast extract, 3% Todd Hewitt media, and 0.25% sucrose to late log phase and collected by centrifugation. Bulk cell pellets were frozen at −70° C. until the material was processed. A 235-g pellet of *M. echinospora* was suspended in 1 liter of 50% acetonitrile-water (60° C.) containing 20 mM $H_2SO_4$ (pH 5 cell suspension). The suspension was adjusted to pH 2.5 with concentrated $H_2SO_4$ and then disrupted using a Bransonic sonicator at ~70% maximum power for 15 min without cooling. The cell extract was cooled on ice, and the cell debris was removed by centrifugation at 6000×g for 15 min at 4° C. The supernatant was reduced to 250 ml using a rotary evaporator and clarified by centrifugation as above. The supernatant contained 240 μmol of thiol by assay with 5,5′-dithiobis(2-nitrobenzoic acid) (Ellman, G. L., 1959, *Arch. Biochem. Biophys.* 82:70).

Next, MSH was recovered from the extract. DTT (250 μmol) was added, and the extract was adjusted to pH 7.9 with concentrated $NH_4OH$. After clarification by centrifugation, the supernatant was passed over a 2-thiopyridine-activated thiolpropyl-agarose column (Newton et al., 1995, *Eur. J. Biochem.*, 230:821–825), the column was eluted with DT7, and the mycothiol was purified by preparative HPLC after derivatization with 5,5′-dithiobis(2-nitrobenzoic acid).

The unbound extract (310 ml) from the thiol affinity column (pH 7.6) was applied directly to a 2.5×1 8-cm Amberlite IRC50 (Mallinckrodt) column that had been prewashed with 3M $NH_4OH$ followed by $H_2O$. The effluent pH was 10.3 when the sample was applied. The column was washed with water and eluted with 350 ml of 1N $NH_4OH$ followed by 550 ml of 3M $NH_4OH$. The fractions from both effluents were found to contain GlcN-Ins as assayed by TLC with ninhydrin detection as previously reported (Maehr, 1980, supra). The fractions containing GlcN-Ins were combined and lyophilized. The residue was redissolved in water (pH~9) and applied to a 1×12-cm AG1-X8 (Bio-Rad, 200–400 mesh) anion exchange column in the hydroxyl form. The column was eluted in water, and the GlcN-Ins-containing fractions were again pooled. The fractions containing GlcN-Ins (RF 0.33) were also contaminated by higher RF ninhydrin-positive materials.

The GlcN-Ins-containing fractions were again combined, dried by lyophilization, and dissolved in 0.1% trifluoroacetic acid, water. This sample was applied to a 20-ml Sep Pak C18 cartridge (Waters) equilibrated in the same solvent. The GlcN-Ins was eluted with 0–5% methanol gradient in aqueous 0.1% trifluoroacetic acid. The GlcN-Ins-containing fractions gave a single ninhydrin spot on TLC, free of the igh RF contaminant. However, amino acid analysis following acid hydrolysis (Newton et al., 1995, supra) revealed that GlcN was a minor: component and that another amine eluting after arginine was a major component. To remove this contaminant, the dried GlcN-Ins-containing fractions were applied to a 1×12-cm Biorex 70 (sodium form, 100–200 mesh, Bio-Rad) column. The GlcN-Ins was eluted in water, and the GlcN-Ins-containing fractions were pooled. Amino acid analysis showed that the basic contaminant had been completely removed. The product gave a small peak at mass 341 (molecular ion) and a major peak at mass 364 (molecular ion plus sodium) on electrospray mass spectroscopy. The $^1H$ NMR was consistent with the expected structure, and all peaks could be assigned by analogy with the spectrum for MSH (Table 3). A stock solution of this material, which contained 0.5 mg of GlcN-Ins by NMR analysis relative to a known concentration of acetone as internal standard, was used for all experiments with GlcN-Ins.

TABLE 3

$^1H$(500 MHz, δ(xJ in Hz)) NMR data for GlcN-Ins and MSmB in $D_2O$ with acetone as the internal reference (δ2.225)

| Assignment | GlcN-Ins | MSmB[a] |
|---|---|---|
| D-glucosamine | | |
| 1 | 5.13 (d), 3.1 | 5.12 (d, 3.5) |
| 2 | 2.76 (dd, 10.4, 3.8) | 3.96 (dd, 10, 3.5) |
| 3 | −3.76 (m) | 3.78 (t, 10) |
| 4 | 3.38 (t, 10) | 3.48 (t, 10) |
| 5 | −3.84 (m) | 3.86 (m) |
| 6 | −3.76 (m) | 3.79 (m) |
|  | 3.84 (m) | 3.88 (m) |
| myo-inositol | | |
| 1′ | 3.58 (dm, 10) | 3.58 (dd, 10, 2) |
| 2′ | 4.20 (t, 2) | 4.19 (t, 2) |
| 3′ | 3.53 (dm, 10) | 3.52 (dd, 10, 2) |
| 4′ | 3.62 (t, 10) | 3.62 (t, 10) |
| 5′ | 3.30 (6, 10) | 3.28 (t, 10) |
| 6′ | 3.63 (t, 10) | 3.76 (t, 10) |

Determination of GlcN and GlcN-Ins—AccQ-Fluor was dissolved in acetonitrile to 10 mM as recommended by the manufacturer. Standard solutions of D-glucosamine-HCl and purified GlcN-Ins were prepared at 3.1 to 200 μM in water. For the derivatization of GlcN and GlcN-Ins, 6 μl of the standard amine was diluted to 30 μl in 200 μmM HEPES (pH 8.0), 15 μl of acetonitrile; 15 μl of 10 mM AccQ-Fluor were added, and the mixture vortexed. After 1 min at room temperature samples were heated for 10 min at 60° C. The samples were diluted 4-fold with water and stored at −70° C. The AccQ-Fluor-derivatized samples were analyzed by HPLC utilizing a Waters 600E solvent delivery system equipped with a Waters WISP Model 710B autoinjector, LDC Fluorometer III, and a Nelson Model 444 data collection system. Separation was obtained on a Beckman Ultrasphere IP (250×4.6 mm) analytical column equipped with a Brownley HPLC guard column containing an OD-GU 5-μm C-18 cartridge using the following linear gradients: 0 min, 100% A (0.1% trifluoroacetic acid in water); 10 min, 100% A; 50 min, 60% B (0.1% trifluoroacetic acid in methanol); 53 in, 100% B; 57 min, 100% B; 60 min, 100% A; 70 min, reinjection. The flow rate was, 1 ml min, and the effluent was monitored by fluorescence with a 254-nm excitation filter and a 370–700-nm emission filter. This protocol is designated HPLC method 5. AccQ-Fluor-derivatized amines had the following retention times: GlcN, 12 min; GlcN-Ins, 24 min.

Figure 12:
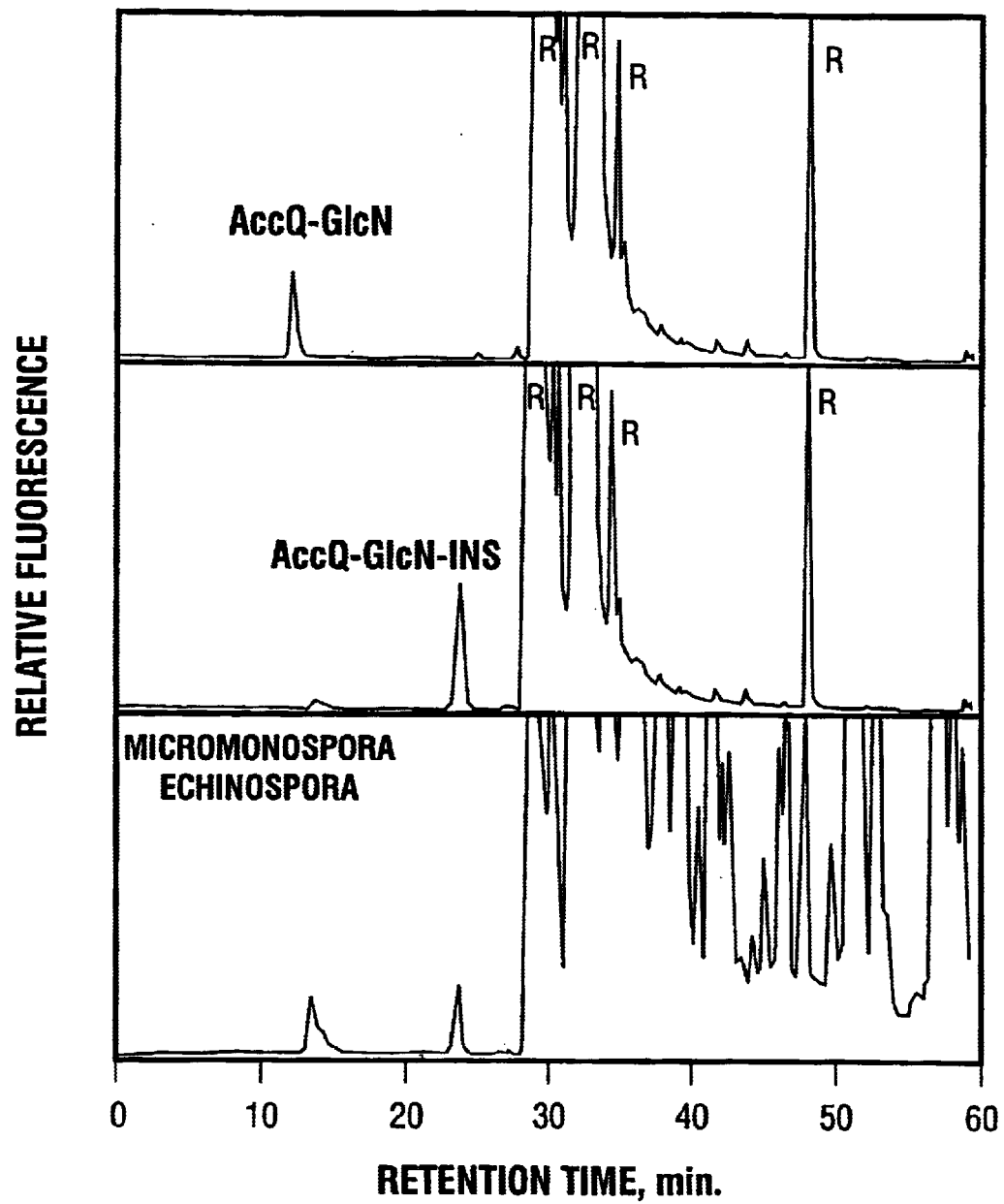
FIG. 12 shows HPLC chromatogram for analysis of aminosugars as their AccQ-Fluor derivatives: (Top) GlcN standard; (Center) GlcN-Ins standard; (bottom) extract of *Micromonospora echinospora*.
Figure 13:
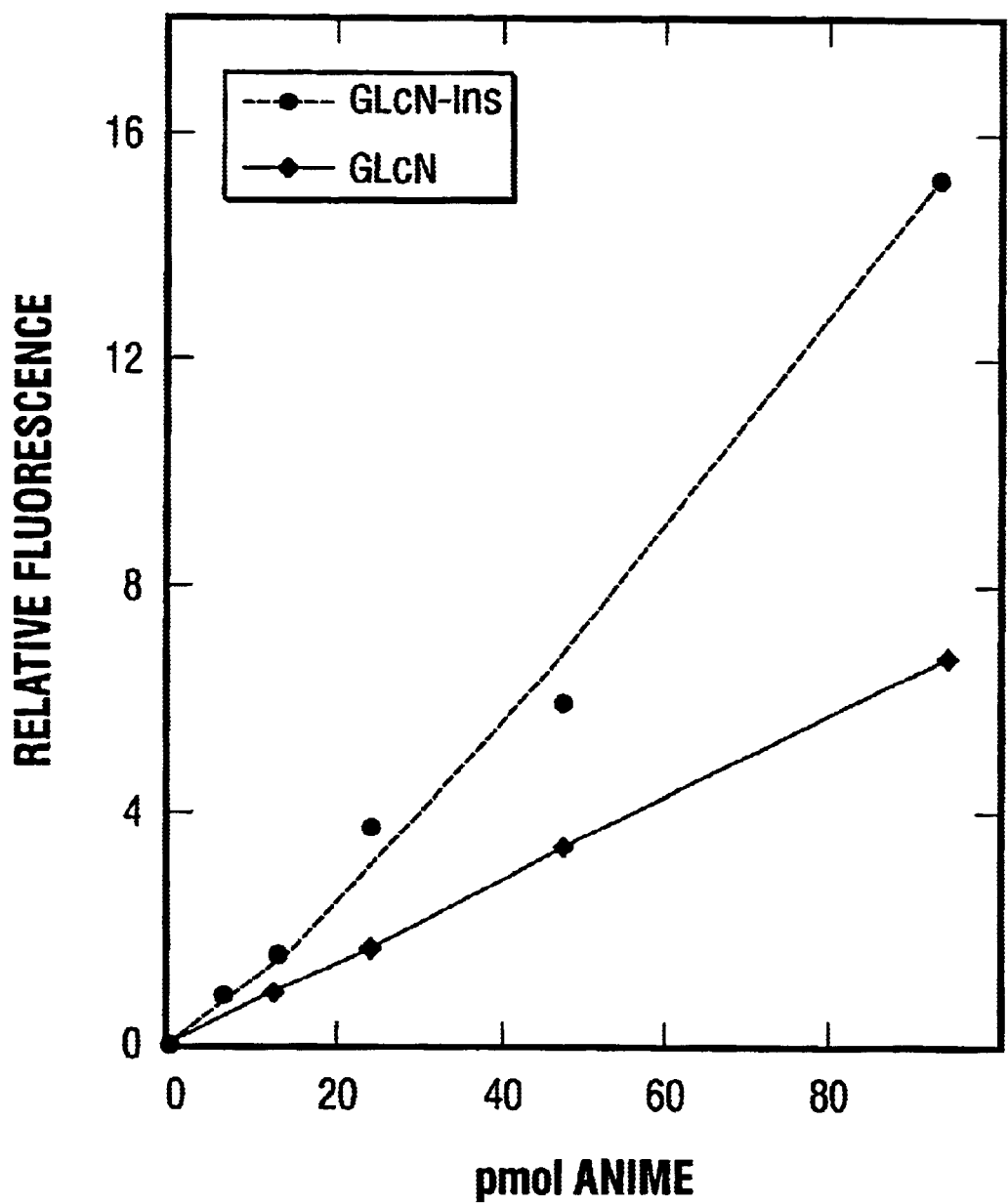
FIG. 13 shows calibration curves for analysis of GlcN (◇) and GlcN-Ins (○).

FIG. 12 shows the chromatograms obtained with GlcN (top panel) and GlcN-Ins (middle panel) standards. FIG. 13 presents a representative calibration curve.

Example 15

Analysis of Selected Bacteria for Mycothiol and Precursors

Organisms and Culture Condition—*M. smegmatis* strains mc$^2$6 and mc$^2$155 and *Staphylococcus aureus* RN450 were kindly provided by Julian Davies, Department of Microbiology and Immunology, University of British Columbia. *Micromonospora echinospora* 14847 was purchased from Norther Regional Research Center (NRRL B-12180), and *Escherichia coli* HB101 was purchased from Promega. *M. smegmatis* cultures were grown in Middlebrook 7H9 broth (0.05% Tween 80 and 0.4% glucose) at 37° C. *S. aureus* and *E. coli* cultures were grown in Trypticase soy broth at 37° C. *M. echinospora* cultures were grown in Todd Hewitt broth (0.5% yeast extract and 0.25% sucrose) at 28° C. All cultures were shaken at 220 rpms.

Determination of Thiols—Cellular thiol levels were analyzed by HPLC after fluorescent labeling of the thiol moiety with mBBr (Newton et al. 1995 supra). Quantitative values for the cellular thiol levels were obtained after correction for any non-thiol fluorescent background identified in control samples in which thiols were blocked by reaction with NEM prior to treatment with mBBr. Standards were prepared by labeling of the commercial (Cys,AcCys) or synthetic (Cys-GlcN. AcCys-GlcN) thiols, or of isolated MSH (Newton et al. 1995 supra). A standard for labeled Cys-GlcN-Ins was obtained by partial hydrolysis of MSmB, purification of CySmB-GlcN-Ins by preparative HPLC, as described below, and quantitation of the standard based upon the absorbance of the bimane label.

Figure 14:
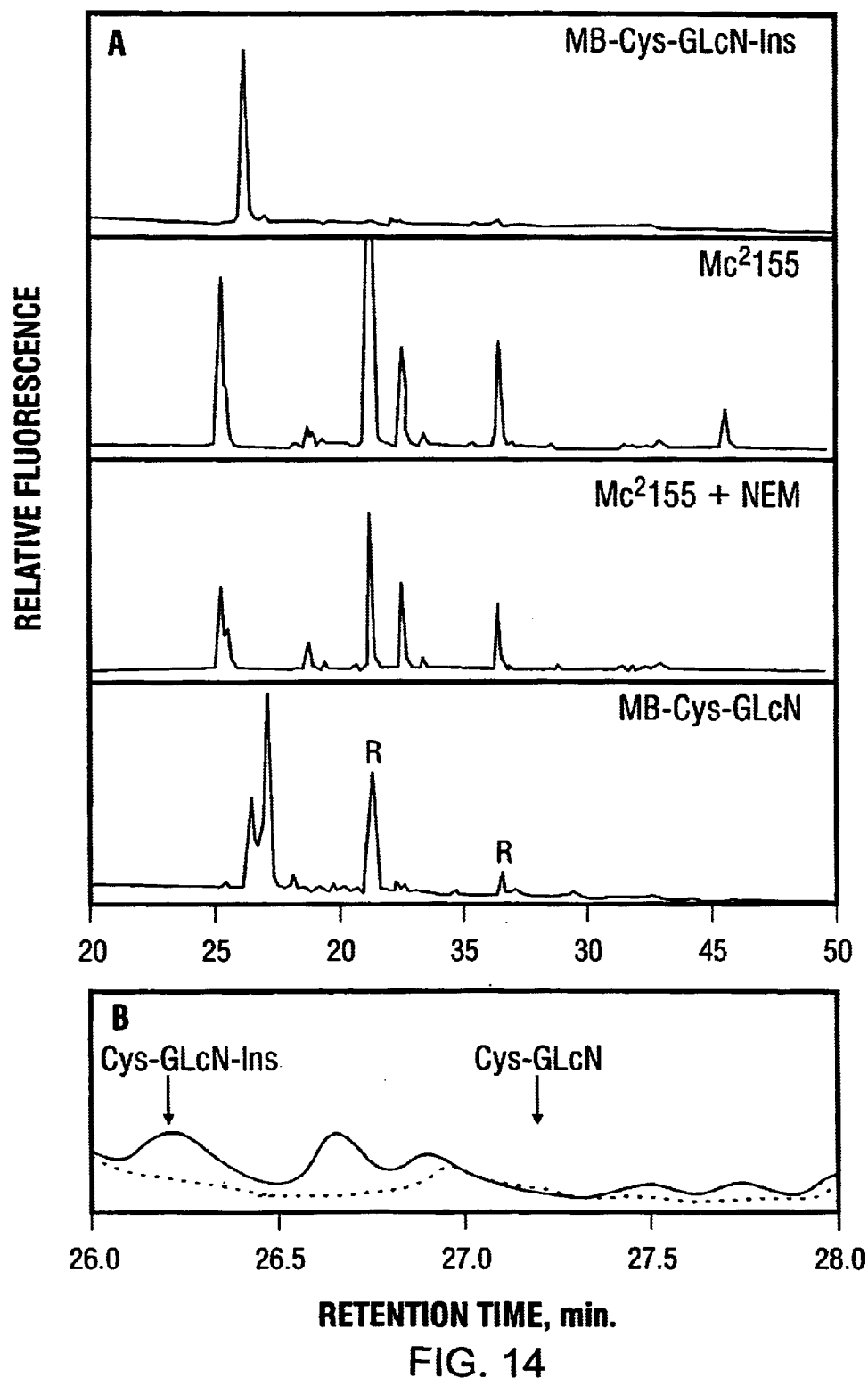
FIG. 14 shows HPLC chromatograms for determination of Cys-GlcN-Ins and Cys-GlcN after labeling with mBBr. A. (1st panel) mB-Cys-GlcN-Ins standard; (2nd pane) mBBr-labeled extract of log phase *M. smegmatis* mc$^2$155 cells; (3rd panel) NEM-treated and mBBr-labeled extract of log phase *M. smegmatis* mc$^2$155 cells showing no-thiol fluorescent components; (4th panel) mB-Cys-GlcN standard. R denotes peakes produced in controls and derived from the reagent mBBr. B. Expaned and amplified (50×) portion of the HPLC chromatogram for a mBBr-labeled sample with a Cys-GlcN-Ins content of 0.07 μmol per g residual dry weight (solid line) and the corresponding NEM control sample (dotted line).
Figure 15:
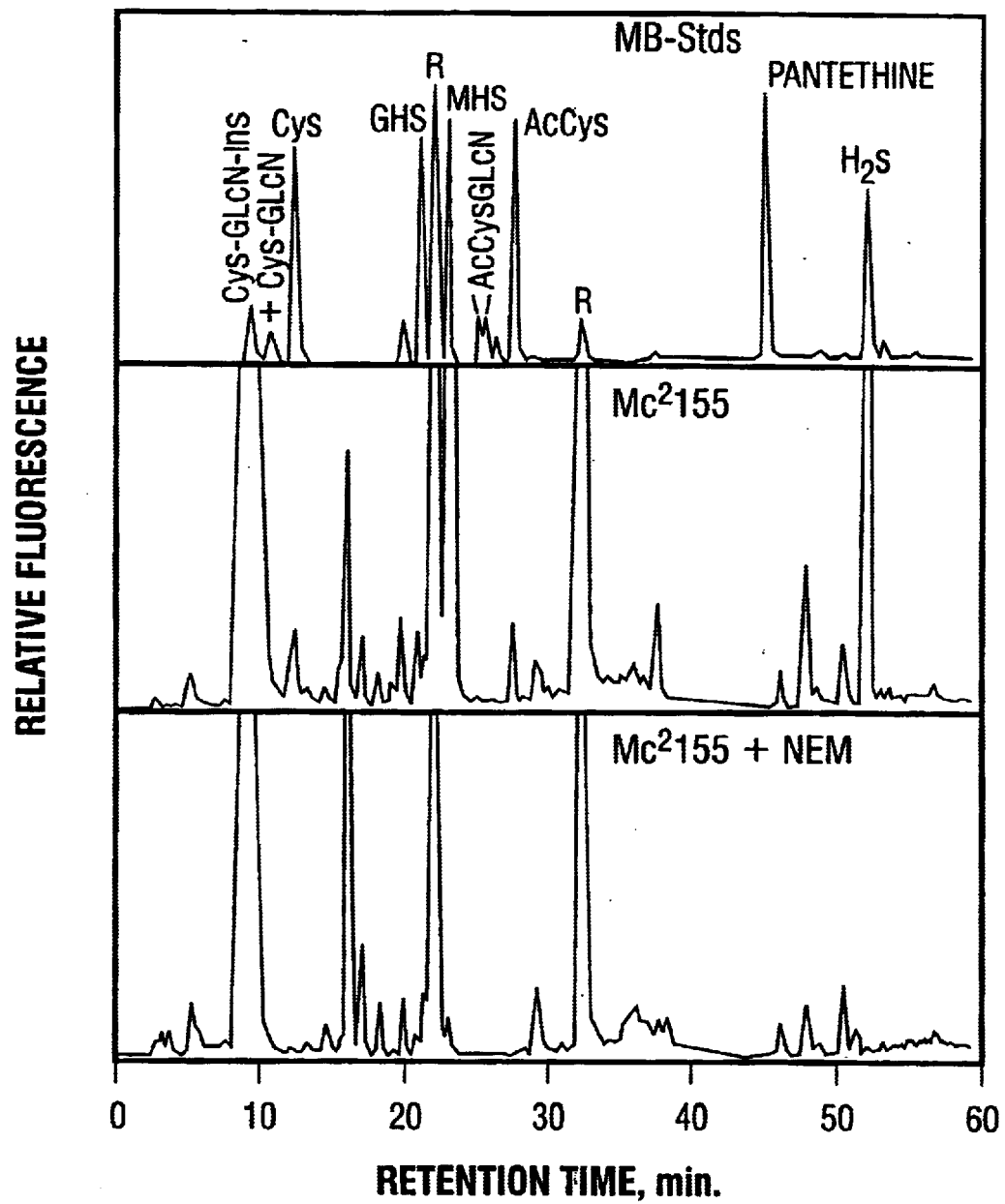
FIG. 15 shows HPLC chromatograms (method 1A) for analysis of thiols: (top panel) mixture of mBBr-labeled thiol standards (R indicates reagent-derived peaks); (middle panel), mBBr-labeled extract of log phase *M. smegmatis* mc$^2$155 cells; (bottom panel), NEM-blocked and mBBr-labeled extract of log phase *M. smegmatis* mc$^2$155 cells showing non-thiol fluorescent components.
Figure 16:
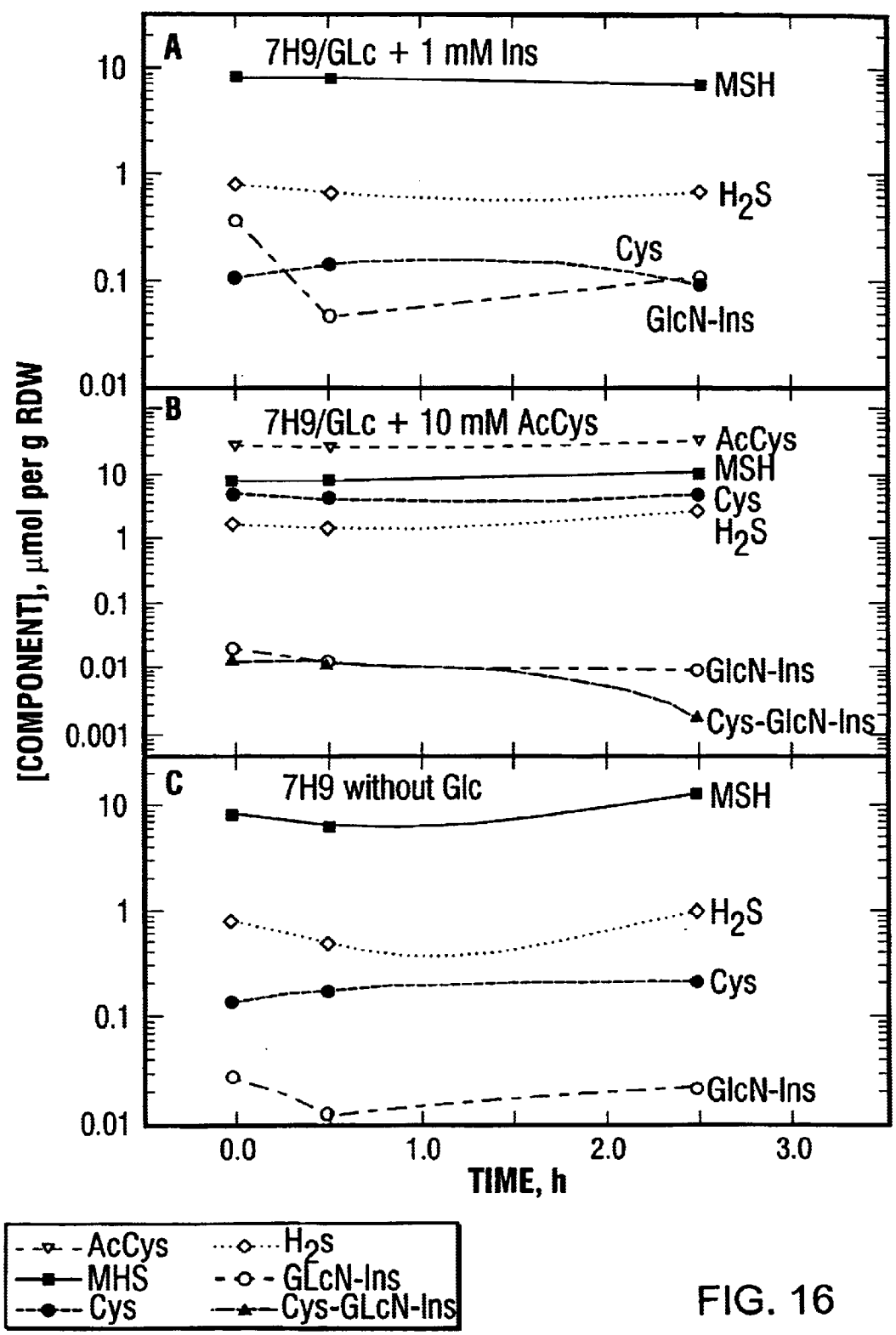
FIG. 16 is a graph illustrating the effect of nutrient supplementation and glucose deprivation upon levels of MSH precursors and intermediates in *M. smegmatis* mc$^2$155 at 37° C.: (A) cells suspended in 7H9 medium with 1% glucose and 1 mM myo-inositol; (B) cells suspended in 7H9 medium with 1% glucose and 10 mM N-acetyl-L-cysteine; (C) cells suspended in 7H9 medium without glucose.

All of these bimane derivatives could not be separated from each other, from reagent derived components, and from fluorescent cellular materials using a single HPLC protocol and many different HPLC separations were tested before two methods were found which provided analyses for the thiols of interest without major coeluting peaks in the NEM control sample. HPLC analysis of Cys, MSH, AcCys-GlcN, AcCys and $H_2S$ was performed using method 1A, a modification of the previously described method 1 (Fahey et al, 1987 supra) with the gradient as follows: 0 min 10% B, 5 min 10% B, 15 min 18% B, 45 min 37% B, 65 min 70% B, 67 min 100% B, 68 min 100% B, 70 min 10% B, and 80 min 10% B (reinjection). For separation of Cys-GlcN-Ins and Cys-GlcN the HPLC conditions were identical to those described above for the determination of GlcN and GlcN-Ins with the following modifications: solvent B was 7.5% methanol in acetonitrile and fluorescence dectection was accomplished with a 370 nm excitation filter and a 418–700 nm emmission filter. FIG. 14 illustrates the analysis used to obtain values for Cys-GlcN-Ins and Cys-GlcN. In cell extracts no peaks were observed for Cys-GlcN and reported values represent the limits of detection (FIG. 14A, second panel). Peaks for Cys-GlcN-Ins were observed with cell extracts as illustrated in FIG. 14B. An unidentified thiol peak of comparable size to the Cys-GlcN-Ins peak and eluting at 26.7 min is also apparent in FIG. 14B. FIG. 15 illustrates the analysis for Cys, AcCys, AcCys-GlcN, MSH, and H2S; Cys-GlcN-Ins and Cys-GlcN were only slightly retained and could not be separated under these conditions. The peaks for Cys and MSH have small coeluting peaks present in the NEM control (FIG. 15, bottom panel) which amounted to 10 and 2%, respectively of the Cys and MSH peaks measured in the sample (FIG. 15, middle panel). In calculating the Cys and MSH content small corrections for these control values were incorporated. Note that the $\alpha$ and $\beta$ epimers of bimane derivatives of Cys-GlcN and AcCys-GlcN interconvert rapidly to give an equilibrium mixture producing two partially resolved peaks with similar retention times (FIG. 15, top panel).

mBBr Derivative of Cys-GkcN-Ins (CySmB-GlcN-Ins)—The bimane derivative of mycothiol (MSmB) was prepared in pure form as described previously (Newton et al., 1995, supra). Approximately 10 mg of MSmB was hydrolyzed in 2 ml of 6 N HCl for 2 h at 60° C., and the hydrolysate was purified by HPLC on a preparative C-18 Vydac column (22×250 mm). The sample was eluted in a 0.1% trifluoroacetic acid in water (mobile phase A) with a 1%/min linear gradient from 0 to 40% B (0.1% trifluoroacetic acid in methanol) at a flow rate of 5 ml min$^{-1}$. The effluent was monitored by fluorescence detection with excitation at 370 nm and emission at 418–700 nm. CySmB-GlcN-Ins was collected at 32 min and repurified twice to minimize CySmB-GlcN contamination. The identity of this peak was confirmed with electrospray mass spectrometry, which yielded a major peak at 657 daltons (molecular ion+Na$^+$). The final yield of 0.63 mg of mB-Cys-GlcN-Ins was estimated assuming $\epsilon$=5300 at 390 nm, the value reported for GS-mB (Kosower, N. S., et al., 1979, *Proc. Natl. Acad. Sci. USA* 76:3382–3386).

Determination of GlcN and GlcN-Ins in cells—To determine GlcN and GlcN-Ins levels in cells a sample of cell suspension grown to mid log phase was chilled on ice and pelleted at 4° C. using a SS34 or GSA rotor in a Sorvall RC-5 centrifuge. The cell pellet was lysed by the addition of 450 $\mu$l of warm acetonitrile and heating at 60° C. for 2 min. Next 490 $\mu$l of water, 10 $\mu$l of 1 M HEPES, pH 8, and 50 $\mu$l of 100 mM NEM in acetonitrile were added, the mixture was heated at 60° C. for 10 min, and the container immediately chilled in ice. The sample was pelleted by brief centrifugation in a microfuge at 4° C. and the supernatant removed to an Eppendorf microcentrifuge tube on ice. A 15 $\mu$l aliquot was immediately taken from the supernatant for derivatization with AccQ-Fluor by addition of 12.5 $\mu$l of 1 M HEPES, pH 8.0, 42.5 $\mu$l of water. 23.8 $\mu$l of acetonitrile, and 31.2 $\mu$l of 10 mM AccQ-Fluor and the mixture vortexed immediately. A second 30 $\mu$l aliquot of cell extract was taken at the same time and prepared in the same fashion except that the volumes of water and acetonitrile added were 35 and 16.8 $\mu$l, respectively. After 1 min at room temperature, the samples were heated for 10 min at 60° C., diluted 4-fold with water, and stored at $-70$° C. The AccQ-Fluor derivatized samples were analyzed by HPLC as stated above in Example 14. FIG. 12 (bottom panel) illustrates the amine analysis from a cell pellet of *Micromonospora echinospora*. The cell pellet was dried in a tared tube to determine the residual dry weight (RDW) of the extract.

Results—Results for analysis of the full range of potential MSH intermediates in a variety bacteria harvested in log phase growth are given in Table 4. Analysis of extracts from *Mycobacterium smegmatis* mc$^2$155 revealed the presence of a measurable GlcN-Ins content. To check whether the values are sensitive to the sample size analyzed, possibly as the result of depletion of the labeling agent by the plethora of amines present in cells, we analyzed 30 $\mu$l of supernatant from extracts (1 ml volume) of *M. smegmatis* mc$^2$155 with increasing sample size from 3.9 to 61 mg RDW of cell pellet residue. For samples sizes up to 30 mg RDW there is an apparent slight decrease in measured GlcN-Ins content with increasing sample size (0.13% per mg RDW) but the change is within the uncertainties in the measurements. However, above 30 mg RDW a marked decrease in measured value was apparent. To prevent underestimates of GlcN-Ins content all quantitative determinations were made with samples less than 30 mg RDW.

*M. smegmatis* mc$^2$6, the parent strain of *M. smegmatis* mc$^2$155, also produced GlcN-Ins in significant amount. Cys was also found, but neither strain appeared to produce comparable amounts of other potential intermediates of MSH metabolism, including AcCys, AcCys-GlcN, Cys-GlcN, or Cys-GlcN-Ins. It had been previously shown that *S. aureus* and *E. coli* did not produce MSH (Newton et al, 1996, supra). These were reexamined using the present methods to ascertain whether they might produce one or more of the intermediates involved in mycothiol biosynthesis and especially GlcN-Ins. The results (Table 4) indicate that neither of these bacteria produce any component of MSH at measurable levels, other than Cys and GlcN.

Variation in Metabolite Levels During Growth—Levels of potential MSH intermediates were determined for *M. smegmatis* mc²155 as a function of growth phase. The MSH level remained remarkably constant through exponential growth and into stationary phase, as did the Cys level at about 1% the MSH level. However, in stationary phase, there did appear to be a significant drop in the GlcN and GlcN-Ins levels and an increase in the $H_2S$ level.

indicating that AcCys significantly inhibits growth under these conditions.

Incubation of cells in the absence of glucose (FIG. 17C) resulted in a decrease in GlcN-Ins level to values 13–30% of normal during the initial 2.5 h incubation, but continuation of the the incubation resulted in a return to normal values by the end of 8 h (data not shown). The MSH level increased to 40% over normal by 2.5 h and remained at that value to 8 h. The value of $A_{600}$ declined slightly (10%) during the 2.5 h incubation period, showing that glucose deprivation arrested cell growth.

TABLE 4

MYCOTHIOL COMPONENT LEVELS IN SELECTED BACTERIA

Content ($\mu$mol/g residual dry weight)*

| Organism | GlcN | GlcN-Ins | $H_2S$ | Cys | AcCys | Cys-GlcN | AcCys-GlcN | Cys-GlcN-Ins | MSH |
|---|---|---|---|---|---|---|---|---|---|
| *M. smegmatis* mc²6 | 0.030 | 0.10 | 1.0 | 0.09 | 0.077 | <0.01 | <0.01 | <0.002 | 7.5 |
| *M. smegmatis* mc²155 | 0.012 ± 0.004 | 0.10 ± 0.04 | 0.87 ± 0.05 | 0.16 ± 0.04 | 0.030 ± 0.004 | <0.003 | <0.08 | 0.008 ± 0.005 | 9.9 ± 1.6 |
| *S. aureus* | 0.027 | <0.001 | 0.36 | 0.35 | 0.002 | <0.03 | <0.004 | <0.05 | <0.04 |
| *E. coli* | 0.024 | <0.001 | 1.7 | 0.09 | <0.0006 | <0.004 | <0.004 | <0.004 | <0.1 |

*Numbers designated with < represent detection limits where no discernable peak was present. Values designated with ± represent measurement of a discrenable peak at the retention time for the indicated component but for which independent verification of the structure was not available; the value represents an upper limit for the content.

Example 16

Effect of Nutrient Supplementation and Deprivation Upon Mycothiol Intermediate Levels To test whether an increase in cellular Ins content would influence the levels of MSH or potential MSH intermediates, we examined *M. smegmatis* mc²155 incubated with Ins. We initially tested Ins uptake by adding 37 $\mu$M $^{14}$C-inositol to a culture at $A_{600}$=1.0 and determining the loss of radiolabel from the medium and its appearance in cells. After 2.5 h, 77% of the counts had been lost from the medium to the cells, showing that *M. smegmatis* efficiently imports inositol. Next we harvested cells after growth to mid log phase, resuspended them at $A_{600}$=1.05 in Middlebrook 7H9 media with glucose and 1 MM Ins at 37° C., and took samples for analysis at 0, 0.5 and 2.5 h (FIG. 17A). The GlcN-Ins content was initially more than 3-fold greater than normal, but fell to about half normal at 0.5 h before returning to normal at 2.5 h. Smaller reciprical changes occurred in the Cys levels, whereas the MSH and $H_2S$ levels did not change to a significant extent. The $A_{600}$ value increased 40% over the 2.5 h incubation, a change comparable to that found for exponential cultures without added Ins.

To test whether changes in cellular Cys levels would influence MSH or MSH intermediates, we incubated cells in medium containing 10 mM AcCys. Since AcCys is readily taken up by passive diffusion we expected this to produce markedly elevated levels of cellular AcCys and, through deacylation, Cys. The results (FIG. 17B) showed this to be the case, the cellular AcCys level was elevated 1000-fold over the normal level and the Cys level was increased 50-fold. This was accompanied by a 5- to 10-fold decrease in GlcN-Ins content whereas the $H_2S$ level roughly doubled. The Cys-GlcN-Ins content was elevated 20-fold over normal immediately after the start of incubation but then fell a factor of 70 over the next 2.5 h. Least affected was the MSH content which was elevated ~40% after 2.5 h. The $A_{600}$ value changed little (5%) over the 2.5 h incubation period

Example 17

Assay of ATP-dependent Ligase Activity with GLCN-Ins Plus CYS/Ac-CYS

Bournemann, et al. (1997 supra) demonstrated the presence of enzyme activity in extracts of *M. smegmatis* capable of converting Cys plus GlcN-Ins to Cys-GlcN-Ins in the presence of ATP and the accompanying production of MSH which was enhanced by acetate or acetyl-CoA. They were unable to assess AcCys as substrate in this reaction because it was rapidly converted to Cys. We conducted analogous assays with an undialyzed supernatant fraction from extraction of *M. smegmatis*.

*M. smegmatis* mc2$^{155}$ was grown to mid-log phase in Middlebrook 7H9 medium with 0.40% glucose and 0.05% Tween. Cells were pelleted and washed with 50 mM sodium phosphate, pH 7.5, containing 1 mM DTT and resuspended in the same buffer at a concentration of 0.25 g wet weight per ml. Cells were lysed by sonication on ice and pelleted by ultracentrifugation at 100,000×g for 30 min in a Beckman tabletop ultracentrifuge. Assay of the supernatant was conducted in a final volume of 600 $\mu$l containing 60 $\mu$l of supernatant, 50 $\mu$M GlcN-Ins, 100 $\mu$M Cys or AcCys, 100 $\mu$M sodium acetate, 1 mM ATP, 1 mM $MgCl_2$, 50 mM sodium phosphate (pH 7.5), 1 mM DTT, and 35 mM each of the protease inhibitors phenylmethanesulfonyl fluoride, N-$\alpha$-p-tosyl-L-phenylalanyl chloromethyl ketone, and N-$\alpha$-p-tosyl-L-lysine chloromethyl ketone. The mixture was incubated at 30° C. and 100 $\mu$l samples removed at 0 and 60 min for thiol analysis. One sample was mixed with 4 $\mu$l 100 mM mBBr and allowed to react 5 min at room temperature before acidification with 0.5 $\mu$l of 5 M methanesulfonic acid to quench the reaction. A second control sample was reacted 5 min with 5 mM NEM prior to treatment with mBBr as above. All samples were subjected to HPLC conditions previously stated for CGI analysis.

Incubation of 100 $\mu$M Cys and 50 $\mu$M GlcN-Ins with 1 mM ATP in phosphate buffer, pH 7.5, containing 1 DTT after addition of cell extract supernatant resulted in an increase in Cys-GlcN-Ins from <0.2 to 26 $\mu$M over 60 min while the MSH content declined from 15 to 13 µM, corresponding to the MSH content present in the undialyzed cell extract. A parallel experiment with 100 µM AcCys in place of Cys resulted in an increase from <0.2 to 20 µM Cys-GlcN-Ins, and no change in MSH content (15 µM); however, marked conversion of AcCys to Cys had occurred by 60 min ([Cys]/[AcCys]~3). If the MSH had increased by as much as 2 µM (10% of the change in Cys-GlcN-Ins) the change would have been detected and this experiment therefore established that conversion of Cys to Cys-GlcN-Ins is at least an order of magnitude faster than conversion of AcCys to MSH under these conditions.

Although the invention has been described with reference to the presently preferred embodiment, it should be understood that various modifications can be made without departing from the spirit of the invention. Accordingly, the invention is limited only by the following claim.

What is claimed is:

1. A method of detecting a member of the taxa actinomycetes in a sample, comprising:
   (a) sequentially incubating with a sample containing a population of about $10^4$ cells of the taxa actinomycetes a thiol-selective reagent that produces maleimidyl derivatives, a purified polyclonal antibody that binds to the maleimidyl derivative of mycothiol, and a reagent for detecting binding of the antibody to sample components for a time sufficient for said antibody to react with said maleimidyl derivative of mycothiol; and
   (b) detecting binding of the antibody with said maleimidyl derivative of mycothiol,
   to indicate the presence of a member of the taxa actinomycetes in the sample.

2. The method of claim 1, wherein said member of the taxa actinomycetes is mycobacteria.

3. The method of claim 1, wherein said sample is selected from the group consisting of a blood sample, a serum sample, a urine sample, a fecal sample, a tissue biopsy, cerebrospinal fluid sample, ascites samples, pleural fluid sample, respiratory secretions, and a sputum sample.

4. The method of claim 1, further comprising
   (c) quantitating said maleimidyl derivative of mycothiol in the sample.

5. The method of claim 1, wherein said detection of binding of the antibody with the mycothiol derivative comprises using a detection reagent directly labeled with a label.

6. The method of claim 5, wherein said label is selected from a fluorophore, a chromophore, a luminophore, a ferritin, a heavy metal and a radioactive label.

7. The method of claim 5, wherein said label is selected from horseradish peroxidases, urease, luciferase and alkaline phosphatase.

8. A kit useful for detecting the presence of mycothiol in a sample, the kit comprising: carrier means being compartmentalized to receive in close confinement therein one or more containers comprising a container containing a polyclonal antibody that binds to a maleimidyl derivative of mycothiol to detect mycothiol in the sample.

9. The kit of claim 8, further comprising a container containing a detection reagent to detect the reaction of the maleimidyl derivative of mycothiol with said antibody to detect the presence of mycothiol.

10. An isolated polyclonal antibody which binds to mycothiol.

* * * * *